United States Patent
Cameron et al.

(10) Patent No.: US 9,417,234 B2
(45) Date of Patent: Aug. 16, 2016

(54) METHODS AND DEVICES FOR DETECTION AND MEASUREMENT OF ANALYTES

(71) Applicant: The University of Toledo, Toledo, OH (US)

(72) Inventors: Brent D. Cameron, Waterville, OH (US); Dong-Shik Kim, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 14/375,929

(22) PCT Filed: Jan. 31, 2013

(86) PCT No.: PCT/US2013/024158
§ 371 (c)(1),
(2) Date: Jul. 31, 2014

(87) PCT Pub. No.: WO2013/116527
PCT Pub. Date: Aug. 8, 2013

(65) Prior Publication Data
US 2015/0024957 A1    Jan. 22, 2015

Related U.S. Application Data

(60) Provisional application No. 61/593,054, filed on Jan. 31, 2012.

(51) Int. Cl.
*G01N 33/543* (2006.01)
*G01N 33/53* (2006.01)
*C12N 15/115* (2010.01)
(Continued)

(52) U.S. Cl.
CPC ............ *G01N 33/54353* (2013.01); *B05D 1/18* (2013.01); *C12N 15/115* (2013.01); *C12Q 1/6825* (2013.01); *G01N 33/5308* (2013.01); *G01N 33/54306* (2013.01); *G01N 33/54373* (2013.01); *G01N 33/54393* (2013.01); *C12N 2310/16* (2013.01); *G01N 2333/76* (2013.01); *G01N 2440/38* (2013.01); *G01N 2610/00* (2013.01)

(58) Field of Classification Search
CPC .................. G01N 33/54353; G01N 33/54306; G01N 33/54373; G01N 33/54393
See application file for complete search history.

(56) References Cited

U.S. PATENT DOCUMENTS

2002/0045277 A1* 4/2002 Schmid ............ G01N 33/54373
436/518
2009/0042237 A1 2/2009 Smith
(Continued)

OTHER PUBLICATIONS

Park et al., "Surface modification of gold electrode with gold nanoparticles and mixed self-assembled monolayers for enzyme biosensors", Korean Journal of Chemical Engineering, 2011, vol. 28, No. 1, pp. 64-70.
(Continued)

*Primary Examiner* — Melanie Y Brown
(74) *Attorney, Agent, or Firm* — MacMillan, Sobanski & Todd, LLC

(57) ABSTRACT

Sensors for target entities having functionalized thereon, at least one aptamer specific to the target entity, and methods of making and using the same are described for use in glycated protein monitoring and/or biomarkers.

10 Claims, 7 Drawing Sheets
(5 of 7 Drawing Sheet(s) Filed in Color)

(51) Int. Cl.
*B05D 1/18* (2006.01)
*C12Q 1/68* (2006.01)

(56) References Cited

U.S. PATENT DOCUMENTS

2010/0284917 A1 11/2010 Küstner et al.
2011/0162979 A1* 7/2011 Shachar ............ G01N 33/5438
205/777.5

OTHER PUBLICATIONS

Pollet et al., "Fiber optic SPR biosensing of DNA hybridization and DNA-protein interactions", Biosensors and Bioelectronics, 2009, vol. 25, pp. 864-869.
Japanese Notification of Reasons for Rejection, Application No. 2014-555710 dated Jul. 7, 2015.

* cited by examiner

METHODS AND DEVICES FOR DETECTION AND MEASUREMENT OF ANALYTES

CROSS-REFERENCE TO RELATED APPLICATIONS

This is a national stage application filed under 35 U.S.C. §371 of international application PCT/US13/24158, filed under the authority of the Patent Cooperation Treaty on Jan. 31, 2013, published; which claims priority to U.S. Provisional Application Ser. No. 61/593,054, filed under 35 U.S.C. §111(b) on Jan. 31, 2012. The entire disclosures of all priority applications are expressly incorporated herein by reference for all purposes.

STATEMENT REGARDING FEDERALLY SPONSORED RESEARCH

The invention was not made with any government support and the government has no rights in the invention.

SEQUENCE LISTING

The instant application contains a Sequence Listing which has been submitted via EFS-web and is hereby incorporated by reference in its entirety. The ASCII copy, created on Jan. 31, 2013, is named 420_53354_SEQ_LIST_D2012-15.txt, and is 3,888 bytes in size.

TECHNICAL FIELD AND INDUSTRIAL APPLICABILITY

The present invention relates to aptamer functionalized surface plasmon resonance (SPR) sensors, methods of making and methods of using the same.

BACKGROUND

The following description provides a summary of information relevant to the present disclosure and is not a concession that any of the information provided or publications referenced herein is prior art to the claimed invention.

The direct detection of blood proteins can benefit a number of scientific and clinical applications, such as in monitoring the ratio of specific protein glycation in diabetes, biomarkers for drug research and environmental monitoring, cancer diagnostics and treatment, and the like. The current clinical and laboratory measurement techniques for blood proteins are boronate affinity immunoassay, high-performance liquid chromatography (HPLC), mass spectrometry and capillary based systems, which are time consuming and costly.

More efficient and fast response measurement methods could greatly benefit and enhance related application areas, especially for developing the next generation of portable handheld diagnostic devices capable of real-time analysis. Several optics-based diagnostic techniques, such as near-infrared spectroscopy, polarimetry, optical coherence tomography, surface plasmon resonance (SPR), Raman and fluorescence spectroscopy have recently been investigated for monitoring blood components. Many of these optical methods, however, are limited in their usefulness due to the effects of confounding substances that may be present in the sample under investigation.

One method for the in vitro selection of nucleic acid molecules that are able to bind with high specificity to target molecules is generally known as SELEX (Systematic Evolution of Ligands by Exponential Amplification) and is described in U.S. Pat. No. 5,475,096 titled "Nucleic Acid Ligands" and U.S. Pat. No. 5,270,163, titled "Nucleic Acid Ligands" each of which is specifically incorporated by reference herein.

Although the currently used SELEX processes are useful, there is always a need for improved processes that allow for the selection of more selective of aptamers to be generated from in vitro selection techniques.

SUMMARY

In one broad aspect, there is provided herein a sensor for detecting the presence of a target entity, comprising an aptamer probe having an amine-terminated end or similar linked to a substrate, wherein, when the sensor is excited by an energy source either: i) in the absence of specific interaction between the target entity and the aptamer probe, a baseline signal is emitted; or ii) in the presence of specific interaction between the target entity and the aptamer probe, a detection signal is emitted, wherein the baseline signal is different from the detection signal, whereby the selective presence of the target entity is detected.

In certain embodiments, the aptamer probe includes a nucleotide sequence which specifically interacts with the target entity.

In certain embodiments, the target entity is one or more of: a large biomolecule, a small biomolecule, an organic molecule, a small molecule, a nucleic acid, a metal ion, a protein, an enzyme, a peptide, a drug, a dye, a cancer cell, a virus, a hormone, or a microorganism. In certain embodiments, the protein is a blood protein.

In certain embodiments, the aptamer probe comprises an aptamer and an attached amine moiety.

In certain embodiments, the aptamer probe includes a SAM linker between the substrate and the amine moiety.

In certain embodiments, the amine-terminated aptamer probe is linked to the substrate by 3-mercaptopropionic acid (MPA).

In certain embodiments, the sensor has a tunable detectable range capable of pM to nM detection, based on the linker characteristics.

In broad aspect, there is provided herein a method of determining if a target entity is present in a sample comprising: i) contacting the sample with a sensor as described herein; ii) exciting the sensor with an energy source; and, iii) determining the strength of emitted signal, thereby determining whether the target entity is present in the sample.

In certain embodiments, the energy source is measured using surface plasmon resonance (SPR).

In certain embodiments, the method has a response time of less than 1 minute. In certain embodiments, the method has a response time of less than 1 minute at about ambient temperature.

In another broad aspect, there is provided herein a kit for the detection of a target entity, comprising: a sensor as described herein; and at least one container containing the sensor, where a sample may be added to the container.

In another broad aspect, there is provided herein a method for making a sensor, comprising: i) immobilizing a self-assembled monolayer (SAM) linker to a substrate; and ii) immobilizing an amine-terminated aptamer to the SAM linker.

In another broad aspect, there is provided herein a method for making a sensor of, comprising: i) functionalizing a substrate with a self-assembled monolayer (SAM) linker; ii) exposing the functionalized substrate of step i) to a composition having an amine moiety sufficient for the amine moiety to be immobilized on the SAM linker; iii) exposing the amine-functionalized substrate of step ii) to at least one aptamer sufficient for the aptamer to be immobilized on the amine moiety; iv) optionally, removing non-specifically immobilized aptamer; and v) exposing the amine-terminated aptamer functionalized substrate of step iii) or iv) to a blocking agent sufficient to block non-occupied SAM sites activated by the amine moiety.

In certain embodiments, the composition having the amine moiety is coupled to one or more of: N-hydroxysuccinimide (NHS) and N-(3-dimethylamnopropyl)-N-ethylcarbodiimide hydrochloride (EDC).

In another aspect, there is provided herein a method for detecting blood proteins using a sensor as described herein.

In another aspect, there is provided herein a method for the ultrasensitive and selective detection and measurement of glycated proteins for application in diabetes therapeutic guidance. In one particular embodiment, the method includes the use of surface plasmon resonance spectroscopy.

In another embodiment, this functionalization method is applicable to other sensing modalities including Raman and fluorescence spectroscopy, and can be used to further improve performance of existing monitoring technologies.

In another aspect, there is provided herein a method to optimize the in vitro selection of aptamers to target specific glycated forms of blood proteins. In one embodiment, a surface functionalization method is used to optimize the sensitivity and selectivity based on the target characteristics.

In another aspect, there is provided herein a method to further reduce effects of confounding substances that may be present in the sample under investigation.

In yet another aspect, there is provided herein a robust, low cost, and portable sensing platform that is capable of achieving similar performance to existing large scale clinical instrumentation. In addition, the integrated platform is useful in a diagnostic device capable of assessing compliance to insulin dependent diabetes therapy. The integrated platform allows for a low cost handheld device that can be used in either a physician's office or in a home environment. The integrated platform also provides an immediate analysis of the data gathered, thus allowing the caregiver and/or patient to assess the patient's long-term glucose regulation compliance.

In another broad aspect, there is provided herein a method for identifying aptamers targeted to a defined site (e.g., glycated protein site), comprising introducing a non-target candidate (e.g., non-glycated candidate) in an at least one round of a systematic evolution of ligands by exponential (SELEX) enrichment protocol, and introducing the non-target candidate in at least a second round of SELEX protocol to remove aptamer candidates with affinity to both glycated and non-glycated protein forms.

In another broad aspect, there is provided herein a surface functionalization method to optimize sensitivity and/or selectivity based on target and/or aptamer characteristics, comprising: using a binary self-assembled monolayer (SAM) formation process using linkages having a desired linking spacing and/or length, wherein at least one of the linkage spacing and/or length are chosen in order to optimize surface plasmon resonance (SPR) sensitivity and selectivity based on target and/or aptamer characteristics.

In another aspect, there is provided herein a method for optimizing sensitivity and/or selectivity of a sensor for one or more analytes, comprising linking one or more types of aptamers to a substrate with a self-assembled monolayer (SAM) linkage, the SAM linkage having a desired linking spacing and/or length to form a functionalized surface on the substrate. The desired linkage spacing and/or length can be chosen in order to optimize at least one of surface plasmon resonance (SPR), Raman spectroscopy, or fluorescence spectroscopy sensitivity and selectivity based on analyte and/or aptamer characteristics.

In certain embodiments, at least one packing density and/or length of the SAM linkage affects a surface plasmon resonance (SPR) signal.

In certain embodiments, linkage is through a binary SAM and reductive desorption process.

In certain embodiments, the desorption process comprising exposing the functionalized surface of the substrate to a material resistant to protein adsorption to prevent non-specific adsorption of protein on the functionalized substrate.

In certain embodiments, the protein adsorption resistant material comprises 1-mercapto-11-undecyl)tri(ethylene glycol) (PEG3).

In certain embodiments, the SAM linkage comprises using a thiol SAM immobilization method, wherein a thiol compound has a carboxy moiety capable of forming a stable bond with the aptamer.

In certain embodiments, the thiol compound comprises dithiobis-N-succinimidyl propionate (DTSP).

In certain embodiments, the SAM linkage is formed using dithiobis-N-succinimidyl propionate (DTSP) and (1-mercapto-11-undecyl)tri(ethylene glycol) (PEG3), wherein PEG3 prevents non-specific adsorption of proteins, and wherein a carboxylic moiety on DTSP forms a stable bonding with the aptamer.

In certain embodiments, a binary SAM thiol solution is used in the SAM linkage.

In certain embodiments, the binary SAM thiol solution is prepared by mixing 1 mM ethanol solutions of 3-mercaptopropionic acid (MPA) and (1-mercapto-11-undecyl)tri(ethylene glycol) (PEG3), while keeping a total concentration of the binary SAMs at about 1 mM.

In certain embodiments, MPA and PEG3 are present at ratio of: about 20:80, about 50:50 or about 80:20.

In certain embodiments, the method further comprises eliminating MPA by reductive desorption, leaving PEG3 intact; and allowing dithiobis-N-succinimidyl propionate (DTSP) to a covalent bond with an amino group on the aptamer, wherein the aptamer attaches to DTSP only, and wherein while PEG3 does not form any bond.

In certain embodiments, the aptamer comprises an amine-modified aptamer capable of being immobilized onto the MPA.

In certain embodiments, the surface has an optimal dynamic in the range of about 5 nM to about 1000 nM.

In certain embodiments, the sensor includes a mixed length spacer layer.

In certain embodiments, the mixed length layer comprises 11-mercaptoundecanoic acid (MUA) combined with 3-mercaptopropionic acid (MPA).

In certain embodiments, a water soluble thiol-containing amino acid capable of directly binding to the surface to form the self-assembly monolayer (SAM) is used. In certain embodiments, the amino acid comprises cysteine.

In another aspect, there is provided herein a method for forming a sensor for one or more analytes, comprising: adsorbing binary components comprised of 3-mercaptopropionic acid (MPA) and (1-mercapto-11-undecyl)tri(ethylene glycol) (PEG3) on a substrate; reductively desorbing MPA from the substrate of step a); immersing the substrate of step b) in a DTSP solution to form a DTSP layer on the substrate; immobilizing at least one type of aptamer on the substrate of step c); and, removing unbound aptamer from the PEG3 on the substrate of step d), thus leaving aptamer attached to the DTSP layer of the substrate.

In another aspect, there is provided herein a method for forming a sensor for one or more analytes, comprising: adsorbing binary components comprised of 3-mercaptopropionic acid (MPA) and (1-mercapto-11-undecyl)tri(ethylene glycol) (PEG3) on a gold surface substrate in an ethanol solution; reductively desorbing MPA from the substrate in a 0.5 M KOH solution, wherein the adsorbed MPA in a phase-separated binary self-assembled monolayer (SAM) of MPA and PEG3 is selectively reduced by applying a potential of −1.2 V for 30 min to the solution; immersing the substrate having the PEG3 layer thereon, in a 1 mM DTSP solution to form a DTSP layer thereon; immobilizing at least one type of aptamer on the substrate; and removing aptamer from the PEG3 on the substrate, thus leaving aptamer attached to the DTSP layer of the substrate.

In certain embodiments, the substrate has a gold surface.

In certain embodiments, the analyte comprises a glycated form of a protein in blood or serum.

In certain embodiments, the method comprises determining a fraction of a specific glycated protein from a total serum protein level.

In certain embodiments, the analyte comprises one or more non-glycated and/or glycated forms of human hemoglobin, albumin, including human serum albumin (HSA), immunoglobulin G (IgG), immunoglobulin M (IgM), fibrinogen, and/or fragments thereof.

In certain embodiments, the analytes comprise at least a first analyte having a different half-life from at least a second analyte, and the method further comprises quantifying the first and second analytes to provide a retrospective judgment regarding levels of the first and second analytes over one or more time periods.

In certain embodiments, the first analyte comprises hemoglobin and the second analyte comprises IgM.

In certain embodiments, the analytes comprise at least a first analyte, at least a second analyte and at least a third analyte, each of the first, second and third analytes having different half-lives, the method further comprising: quantifying the first, second and third analytes to provide a retrospective judgment regarding levels of the first, second and third analytes over one or more time periods.

In certain embodiments, the first analyte comprises hemoglobin, the second analyte comprises IgM and the third analyte comprises albumin.

In certain embodiments, the method is useful for monitoring past average glucose levels, the method comprising: contacting a sensor formed by a method described herein with a blood sample; determining an amount of the glycated form of the protein in the blood; and correlating an amount of the protein present in the blood sample in the glycated form to a control glucose level for a given time frame.

In certain embodiments, the amount of the glycated form of the protein is determined using surface plasmon resonance (SPR).

In another aspect, there is provided herein a sensor for detecting the presence of one or more analytes, wherein the sensor is formed by any one of the methods described herein.

In certain embodiments, the aptamer includes a nucleotide sequence capable of interacting with a specific analyte.

In certain embodiments, the sensor is capable of interacting with one or more analytes selected from: a large biomolecule, a small biomolecule, an organic molecule, a small molecule, a nucleic acid, a metal ion, a protein, an enzyme, a peptide, a drug, a dye, a cancer cell, a virus, a hormone, or a microorganism.

In certain embodiments, the analyte is one or more of: a biological sample, an environmental sample, a chemical sample, a pharmaceutical sample, a food sample, an agricultural sample, and a veterinary sample.

In certain embodiments, the protein is a blood protein.

In certain embodiments, the sensor has a tunable detectable range capable of pM to nM detection, based on the linker characteristics.

In certain embodiments, the sensor has a response time of less than 1 minute.

In certain embodiments, the sensor has a response time of less than 1 minute at about room temperature.

In another aspect, there is provided herein a kit for the detection of one or more analytes, comprising: a sensor as described herein; and at least one container containing the sensor, where a sample may be added to the container.

In another aspect, there is provided herein a method for reducing an effect of at least one confounding substance that may be present in a sample, comprising: incorporating one or more hydrophilic groups in non-binding locations on the substrate sufficient to substantially reduce/prevent non-specific adsorption of the confounding substance, linking an aptamer to the substrate with a self-assembled monolayer (SAM) linkage, the SAM linkage having a desired linking spacing and/or length to form a functionalized surface on the substrate, and detecting aptamer binding response by SPR sensor at separation distance beyond normal SPR detection limit.

Also described herein is a method which uses surface plasmon resonance (SPR) spectroscopy and custom developed aptamer-based functionalized sensor surfaces to detect and/or quantify one or more target molecules, or fragments thereof, in a test environment. The method allows for the detection and/or measurement of such molecules with a large range of half-lives, including but not limited to target molecules with half-lives shorter than that of hemoglobin. Furthermore, the method can be conducted without the use of tags or labels such as fluorescent dyes, or photocrosslinking. The method also has low sample consumption, and provides a fast response time (generally seconds), making it useful for application in assessing glycemic compliance.

In another aspect, there is provided herein a sensor, comprising: one or more types of aptamers linked to a substrate with a self-assembled monolayer (SAM) linkage, the SAM linkage having a desired linking spacing and/or length to form a functionalized surface on the substrate, the desired linkage spacing and/or length being chosen in order to optimize at least one of surface plasmon resonance (SPR), Raman spectroscopy, or fluorescence spectroscopy sensitivity and selectivity based on analyte and/or aptamer characteristics.

In certain embodiments, the at least one packing density and/or length of the SAM linkage affects a surface plasmon resonance (SPR) signal.

In certain embodiments, the linkage is through a binary SAM and reductive desorption process.

In certain embodiments, the functionalized surface of the substrate has been exposed to a material resistant to protein adsorption sufficient to inhibit non-specific adsorption of protein on the functionalized surface.

In certain embodiments, the protein adsorption resistant material comprises 1-mercapto-11-undecyl)tri(ethylene glycol) (PEG3).

the SAM linkage comprises a thiol compound having a carboxy moiety capable of forming a stable bond with the aptamer.

In certain embodiments, the thiol compound comprises dithiobis-N-succinimidyl propionate (DTSP).

In certain embodiments, the SAM linkage is formed using dithiobis-N-succinimidyl propionate (DTSP) and (1-mercapto-11-undecyl)tri(ethylene glycol) (PEG3), wherein PEG3 prevents non-specific adsorption of proteins, and wherein a carboxylic moiety on DTSP forms a stable bonding with the aptamer.

In certain embodiments, a binary SAM thiol solution is used in the SAM linkage.

In certain embodiments, the binary SAM thiol solution is prepared by mixing 1 mM ethanol solutions of 3-mercaptopropionic acid (MPA) and (1-mercapto-11-undecyl)tri(ethylene glycol) (PEG3), while keeping a total concentration of the binary SAMs at about 1 mM.

In certain embodiments, the MPA and PEG3 are present at ratio of: about 20:80, about 50:50 or about 80:20.

In certain embodiments, the MPA has been eliminated by reductive desorption, leaving PEG3 intact; and dithiobis-N-succinimidyl propionate (DTSP) has bonded with an amino group on the aptamer, and PEG3 does not form any bond.

In certain embodiments, the aptamer comprises an amine-modified aptamer capable of being immobilized onto of 3-mercaptopropionic acid (MPA).

In certain embodiments, the surface has an optimal dynamic in the range of about 5 nM to about 1000 nM.

In certain embodiments, the sensor includes a mixed length spacer layer.

In certain embodiments, the mixed length layer comprises 11-mercaptoundecanoic acid (MUA) combined with 3-mercaptopropionic acid (MPA).

In certain embodiments, the SAM linkage comprises a water soluble thiol-containing amino acid capable of directly binding to the surface of the substrate.

In certain embodiments, the amino acid comprises cysteine.

In another aspect, there is provided herein a sensor where at least the surface of the substrate is gold.

In certain embodiments, the sensor is configured for sensing an analyte comprised of a glycated form of a protein in blood.

In certain embodiments, the sensor is configured for determining a fraction of a specific glycated protein from a total serum protein level.

In certain embodiments, the analyte comprises one or more of: human hemoglobin, albumin, including human serum albumin (HSA), immunoglobulin G (IgG), immunoglobulin M (IgM), fibrinogen, and/or fragments thereof, the analyte being in glycated or non-glycated forms.

In certain embodiments, the analytes comprise at least a first analyte having a different half-life from at least a second analyte.

In certain embodiments, the first analyte is comprised of hemoglobin and the second analyte is comprised of immunoglobulin M (IgM); and, wherein either of the first analyte or the second analyte is present in a glycated form or a non-glycated form.

In certain embodiments, the analytes comprise at least a first analyte, at least a second analyte and at least a third analyte, each of the first, second and third analytes having different half-lives.

In certain embodiments, the first analyte is comprised of hemoglobin, the second analyte is comprised of IgM, and the third analyte is comprised of albumin; wherein one or more of the first analyte, the second analyte or the third analyte is present in a glycated form or a non-glycated form.

In another aspect, there is provided herein a use of any one of the sensors described herein for monitoring past average blood analyte levels, by: contacting a sensor formed by a method described herein with a blood sample; determining an amount of the glycated form of the analyte in the blood; and correlating an amount of the analyte present in the blood sample analyte in a glycated form of to a control level for a given time frame.

In certain embodiments, the amount of the glycated form of the protein is determined using surface plasmon resonance (SPR).

In certain embodiments, the aptamer includes a nucleotide sequence capable of interacting with a specific analyte.

In certain embodiments, the sensor is capable of interacting with one or more analytes selected from: a large biomolecule, a small biomolecule, an organic molecule, a small molecule, a nucleic acid, a metal ion, a protein, an enzyme, a peptide, a drug, a dye, a cancer cell, a virus, a hormone, or a microorganism.

In certain embodiments, the analyte is one or more of: a biological sample, an environmental sample, a chemical sample, a pharmaceutical sample, a food sample, an agricultural sample, and a veterinary sample.

In certain embodiments, the analyte is a blood protein.

In certain embodiments, the sensor has a tunable detectable range capable of pM to nM detection, based on the linker characteristics.

In certain embodiments, the sensor has a response time of less than 1 minute.

In certain embodiments, the sensor has a response time of less than 1 minute at about ambient temperature.

In certain embodiments, the sensor includes an aptamer where the aptamer comprises a DNA sequence having at least 70% identity to the entire sequence of any one of SEQ ID NOS: 4, 5, 6, 7, 8, 9, 10, 11, 12, 13, 14 and 15.

In another aspect, there is provided herein a kit for the detection of one or more analytes, comprising: any one or more of the sensors described herein; and at least one container including the sensor, where a sample may be added to the container.

In certain embodiments, the kit further comprises one or more solid supports, one or more separating agents for separating the sensor from an elute, and one or more reagents for separating an aptamer from the sensor.

In another aspect, there is provided herein a method of identifying a single target-site binding aptamer from a pool of nucleic acids having single-target-site-binding-aptamers and non-target-protein-binding-aptamers therein, comprising:
  a) adding to the pool of nucleic acids, a single-site-target-protein-complex, wherein both the single-target-site-binding-aptamers and the non-target-protein-binding-aptamers present in the pool bind to the single-site-target-protein-complex, and form a single-target-site-binding-aptamer+non-target-protein-binding-aptamer+single-site-target-protein-complex;
  b) separating the single-target-site-binding-aptamer+non-target-protein-binding-aptamer+single-site-target-protein-complex from the pool;
  c) eluting the single-target-site-binding-aptamers and the non-target-protein-binding-aptamers from the single-site-target-protein-complex;
  d) adding to the elute of the previous step, a non-target-protein-complex, wherein the non-target-protein-binding-aptamers present in the elute of step c) bind to the non-target-protein-complex, and form a non-target-protein-binding-aptamer+non-target-protein-complex;

e) separating the non-target-protein-binding-aptamer+non-target-protein-complex from the elute of the previous step, leaving the single-target-site-binding-aptamer in the elute; and, f) separating the single-target-site-binding-aptamers from the elution; optionally, further amplifying the single-target-site-binding-aptamers.

In certain embodiments, the single-target-site-binding-aptamers are used to select for one of: hemoglobin, immunoglobulin G (IgG), immunoglobulin M (IgM) and albumin.

In certain embodiments, the single-target-site-binding-aptamers are selected from: SEQ ID NOs: 3, 4, 5, 6, 7, 8, 9, 10, 11, 12, 13, 14 and 15.

In certain embodiments, the single-site-target-protein is immobilized on a solid support.

In certain embodiments, the non-target-protein-complex is immobilized on a solid support.

In certain embodiments, the solid support comprises a magnetic bead, a chromatographic matrix, a microtiter dish or an array.

In another aspect, there is provided herein an aptamer that binds to glycated hemoglobin, wherein the aptamer comprises a nucleic acid sequence selected from the group consisting of SEQ ID NOs: 4 and 5.

In certain embodiments, the glycated hemoglobin is human hemoglobin.

In certain embodiments, the aptamer has a dissociation constant for human hemoglobin of 100 nM or less.

In another aspect, there is provided herein an aptamer described herein that binds to glycated hemoglobin, wherein the aptamer comprises a nucleic acid sequence selected from the group consisting of SEQ ID NOs: 4 and 5, and one or more of: a 5'-linker and a 3'-linker.

In certain embodiments, the linker is a self-assembled monolayer (SAM).

In another aspect, there is provided herein, an aptamer with at least 70% identity to the entire sequence of any one of SEQ ID NOs: 4 and 5 and that binds to human glycated hemoglobin.

In another aspect, there is provided herein a composition of matter comprising a self-assembled monolayer (SAM) conjugated to a nucleic acid aptamer molecule comprising a polynucleotide sequence capable of specifically binding a region of glycated hemoglobin, wherein the polynucleotide sequence is selected from the group consisting of SEQ ID NOs:4 and 5.

In another aspect, there is provided herein an aptamer that binds to non-glycated hemoglobin, wherein the aptamer comprises a nucleic acid sequence selected from the group consisting of SEQ ID NOs: 6 and 7.

In certain embodiments, the non-glycated hemoglobin is human hemoglobin.

In certain embodiments, the aptamer has a dissociation constant for human hemoglobin of 100 nM or less.

In another aspect, there is provided herein aptamer that binds to non-glycated hemoglobin, wherein the aptamer comprises a nucleic acid sequence selected from the group consisting of SEQ ID NOs:6 and 7, and one or more of: a 5'-linker and a 3'-linker.

In certain embodiments, the linker is a self-assembled monolayer (SAM).

In another aspect, there is provided herein an aptamer with at least 70% identity to the entire sequence of any one of SEQ ID NOs:6 and 7 and that binds to human non-glycated hemoglobin.

In another aspect, there is provided herein a composition of matter comprising a self-assembled monolayer (SAM) conjugated to a nucleic acid aptamer molecule comprising a polynucleotide sequence capable of specifically binding a region of non-glycated hemoglobin, wherein the polynucleotide sequence is selected from the group consisting of SEQ ID NOs:6 and 7.

In another aspect, there in provided herein an aptamer that binds to glycated serum albumin, wherein the aptamer comprises a nucleic acid sequence selected from the group consisting of SEQ ID NOs:3, 8 and 9.

In certain embodiments, the glycated serum albumin is human glycated serum albumin.

In certain embodiments, the aptamer has a dissociation constant for human glycated serum albumin of 100 nM or less.

In another aspect, there is provided herein an aptamer that binds to glycated serum albumin, wherein the aptamer comprises a nucleic acid sequence selected from the group consisting of SEQ ID NOs:3, 8 and 9, and one or more of: a 5'-linker and a 3'-linker.

In certain embodiments, the linker is a self-assembled monolayer (SAM).

In another aspect, there is provided herein an aptamer with at least 70% identity to the entire sequence of any one of SEQ ID NOS:3, 8 and 9, and that binds to human glycated serum albumin.

In another aspect, there is provided herein a composition of matter comprising a self-assembled monolayer (SAM) conjugated to a nucleic acid aptamer molecule comprising a polynucleotide sequence capable of specifically binding a region of glycated serum albumin, wherein the polynucleotide sequence is selected from the group consisting of SEQ ID NOs:3, 8 and 9.

In another aspect, there is provided herein an aptamer that binds to non-glycated serum albumin, wherein the aptamer comprises a nucleic acid sequence selected from the group consisting of SEQ ID NOs:10, 11, 12, 13, 14 and 15.

In certain embodiments, the non-glycated serum albumin is human glycated serum albumin.

In certain embodiments, the aptamer has a dissociation constant for human non-glycated serum albumin of 100 nM or less.

In another aspect, there is provided herein an aptamer that binds to non-glycated serum albumin, wherein the aptamer comprises a nucleic acid sequence selected from the group consisting of SEQ ID NOs: 10, 11, 12, 13, 14 and 15, and one or more of: a 5'-linker and a 3'-linker.

In certain embodiments, the linker is a self-assembled monolayer (SAM).

In another aspect, there is provided herein an aptamer with at least 70% identity to the entire sequence of any one of SEQ ID NOS: 10, 11, 12, 13, 14 and 15, and that binds to human non-glycated serum albumin.

In another aspect, there is provided herein a composition of matter comprising a self-assembled monolayer (SAM) conjugated to a nucleic acid aptamer molecule comprising a polynucleotide sequence capable of specifically binding a region of non-glycated serum albumin, wherein the polynucleotide sequence is selected from the group consisting of SEQ ID Nos. 10, 11, 12, 13, 14 and 15.

In certain embodiments, the aptamer comprises at least one chemical modification.

In certain embodiments, the modification is selected from the group consisting of: a chemical substitution at a sugar position, a chemical substitution at an internucleotide linkage, and a chemical substitution at a base position.

In another aspect, there is provided herein a test reagent comprising an effective amount of an aptamer described herein, or a salt thereof, and a support therefor.

In another aspect, there is provided herein a kit comprising at least one aptamer as described herein.

In certain embodiments, the aptamer is PEGylated.

In certain embodiments, the PEGylated aptamer molecule includes 1-mercapto-11-undecyl)tri(ethylene glycol) (PEG3).

In certain embodiments, the SAM linkage is formed using dithiobis-N-succinimidyl propionate (DTSP) and (1-mercapto-11-undecyl)tri(ethylene glycol) (PEG3).

In certain embodiments, the aptamer comprises at least one chemical modification.

In certain embodiments, the modification is selected from the group consisting of: a chemical substitution In certain embodiments, at a sugar position, a chemical substitution at an internucleotide linkage, and a chemical substitution at a base position.

A test reagent comprising an effective amount of one or more aptamers described herein or a salt thereof, and a support therefor.

A kit comprising one or more aptamers described herein.

In another aspect, there are provided herein purified and isolated non-naturally occurring DNA sequences selected from the group consisting of SEQ ID NOs: 3, 4, 5, 6, 7, 8, 9, 10, 11, 12, 13, 14 and 15.

In another aspect, there is provided herein a method for reducing an effect of at least one confounding substance that may be present in a sample, comprising: a) incorporating one or more hydrophilic groups in non-binding locations on the substrate sufficient to substantially reduce/prevent non-specific adsorption of the confounding substance, b) linking an aptamer to the substrate with a self-assembled monolayer (SAM) linkage, the SAM linkage having a desired linking spacing and/or length to form a functionalized surface on the substrate, and c) detecting aptamer binding response by SPR sensor at separation distance beyond normal SPR detection limit.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

(FIG. 11a) co-adsorption of MPA and PEG3 on Au; (FIG. 11b) reductive desorption of MPA; (FIG. 11c) adsorption of DTSP; (FIG. 11d) aptamer immobilization; and, (FIG. 11e) removing aptamer from PEG3.

DETAILED DESCRIPTION

Figure 1:
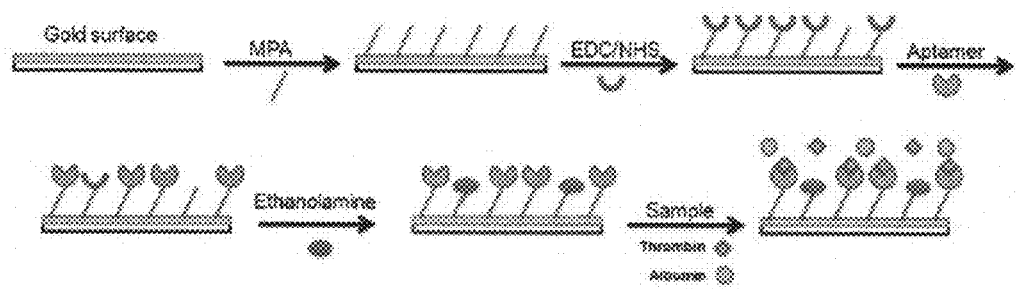
FIG. 1: Schematic diagram of a sensing surface functionalization method.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

DEFINITIONS

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

As used in this specification, including the claims, the singular forms "a," "an," and "the" include plural references, unless the content clearly dictates otherwise, and are used interchangeably with "at least one" and "one or more." That is, a reference to "an aptamer" includes mixtures of aptamers, reference to "nucleic acids" includes mixtures of nucleic acids, and the like.

As used herein, the term "about" represents an insignificant modification or variation of the numerical values such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The term "aptamers" as used here indicates oligonucleic acid or peptide molecules that are capable to bind a specific target entity. In general, aptamers are artificial oligonucleotides which can serve as antibody mimics because of their high affinity and selectivity for various target compounds ranging from small molecules, such as drugs and dyes, to complex biological molecules such as enzymes, peptides, and proteins. Custom aptamers can be identified from random oligonucleotide libraries for specific target compounds by an in vitro iterative process called Systematic Evolution of Ligands by Exponential Amplification (SELEX). For examples of SELEX processes see U.S. Pat. Nos. 5,270,163; 5,475,096; and 5,567,588, which are incorporated herein by reference in their entirety.

Aptamers can form a 3D structure serving as receptors specific to their target compounds similar to antibodies. Aptamers also have a number of advantages over antibodies such as a tolerance to wide ranges of pH and salt concentrations, heat stability, ease of synthesis, and cost efficiency. The specificity and affinity of aptamers are comparable, if not higher, to antibodies. Aptamers are also capable of being reversibly denatured for the release of target compounds, which makes the aptamers especially useful receptors for biosensing applications.

For example, aptamers can be comprised of single-stranded (ss) oligonucleotides and/or be chemically synthesized peptides that have been engineered through repeated rounds of in vitro selection, or equivalent techniques identifiable by a skilled person, to bind to various targets.

An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers may have either the same number or a different number of nucleotides. Aptamers may be DNA or RNA and may be single stranded, double stranded, or contain double stranded regions.

It is to be understood that that affinity interactions between and aptamer and an analyte or target are a matter of degree. That is, the "specific binding affinity" of an aptamer for its target means that the aptamer binds to its target generally with a much higher degree of affinity than such aptamer may binds to other, non-target, components in a mixture or sample.

As used herein the term "amplification" or "amplifying" means any process or combination of process steps that increases the amount or number of copies of a molecule or class of molecules.

As used herein, "pool" is a mixture of nucleic acids of differing sequence from which to select a desired ligand. The source of a pool can be from naturally-occurring nucleic acids or fragments thereof, chemically synthesized nucleic acids, enzymatically synthesized nucleic acids or nucleic acids made by a combination of the foregoing techniques. Modified nucleotides, such as nucleotides with a detectable label, reactive groups or other modifications, can be incorporated into the pool. In certain embodiments, a SELEX process and/or the improved SELEX method described herein can be used to produce a pool. A pool can also comprise nucleic acids with one or more common structural moieties, such that the nucleic acids can be separated by structure, and not by chemical, size, or other separation method. As used herein, a pool is also sometimes referred to as a "library" or a "candidate or nucleic acid mixture." For example, an "RNA pool" refers to a candidate mixture comprised of RNA.

As used herein, "nucleic acid," "oligonucleotide," and "polynucleotide" are used interchangeably to refer to a polymer of nucleotides of any length, and such nucleotides may include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules.

The term "sensor" as used herein indicates a device that measures a physical quantity and converts it into a signal which can be read by an observer or by an instrument. As is understood, a sensor is calibrated against known standards. Accordingly, a sensor can be used to capture a target entity by exploiting the affinity of aptamer to the target entity, and can be detected using techniques identifiable by a skilled person upon reading of the present disclosure.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: spectra or images from a target of interest or a probe attached to the target.

The term "labeling agent," "label," or "detectable moiety", or "detectable element" or "detectable component" refers to one or more reagents that can be used to detect a target molecule/aptamer complex. A detectable moiety or label is capable of being detected directly or indirectly.

The terms "target," "target entity" and "analyte" may be used herein interchangeably, and generally refer to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, amino acids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The terms "polypeptides," "peptides," and "proteins" are intended to encompass polymers of amino acids of any length, whether linear or branched, that may or may not be modified naturally or by intervention, such as by glycosylation, lipidation, acetylation, phosphorylation, disulfide bond formation, conjugation, or other manipulation or modification.

The term "solid support" means any substrate having a surface to which molecules may be attached, directly or indirectly, through either covalent or non-covalent bonds. The substrate materials may be naturally occurring, synthetic, or a modification of a naturally occurring material. Solid support materials may include magnetic beads, or any other materials that are capable of having one or more functional groups, such as any of an amino, carboxyl, thiol, or hydroxyl functional group, for example, incorporated on its surface. The solid support may take any of a variety of configurations ranging from simple to complex and can have any one of a number of shapes, including beads, disks, particles, plates, rods, strips, tubes, wells, and the like. The surface may be relatively planar (e.g., a slide), spherical (e.g., a bead), cylindrical (e.g., a column), or grooved.

The term "separating" means any process whereby one or more components of a mixture are separated from other components of the mixture. For example, aptamers bound to target molecules can be separated from other nucleic acids that are not bound to target molecules and from non-target molecules. That is, a separation process or step allows for the separation of all the nucleic acids in a candidate mixture into at least two pools based on their relative affinity and/or dissociation rate to the target molecule. The separation process can be accomplished by various methods. For example, magnetic beads upon which target molecules are conjugated can also be used to separate aptamers in a mixture. As another example, surface plasmon resonance (SPR) technology can be used to separate nucleic acids in a mixture by immobilizing a target on a sensor chip and flowing the mixture over the chip, wherein those nucleic acids having affinity for the target can be bound to the target, and the remaining nucleic acids can be washed away.

The term "sample" as used herein refers to a mixture, gas, or substance that may or may not comprise a target or analyte. Samples include but are not limited to biological samples, such as blood, sputum, breath, urine, semen, saliva, amniotic fluid, meningeal fluid, glandular fluid, nipple aspirate, lymph fluid, bronchial aspirate, joint aspirate, synovial fluid, cellular extract, cerebrospinal fluid, homogenized solid material from stool or tissue samples, bacterial culture, viral culture, or experimentally-separated fractions thereof.

The term "non-target" refers to molecules in a sample that form a non-specific complex with an aptamer. It will be appreciated that a molecule that is a non-target for a first aptamer may be a target for a second aptamer. Similarly, a molecule that is a target for a first aptamer may be a non-target for a second aptamer.

GENERAL DESCRIPTION

The methods and devices described provide a system that has both the desired high sensitivity and specificity to be able to detect glycated proteins in a desired test environment and at sensitive concentrations.

In a particular aspect, the method includes determining the fraction of a specific glycated protein from the total serum protein level. Non-limiting examples of such proteins include: human hemoglobin, albumin (such as human serum albumin (HSA)), and IgM proteins.

Two common glycated proteins found in the body are hemoglobin A1c (HbA1c) and immunoglobulin M (IgM) (which is a basic antibody present on B cells). Both HbA1c and IgM have different half-lives in the body; e.g., ~6-8 weeks for HbA1c, and ~1 week for IgM. Therefore, quantification of these glycated proteins in serum provides a retrospective judgment regarding glycemic control over both a shorter and longer term. The present method overcomes one of the primary shortcomings of other tests where only one type of glycated serum protein could be detected; and consequently, any compliance assessment with regard to glucose control was limited to only one fixed time period. It is also to be noted that the present method overcomes other shortcomings that limit the assay results, such as interferences from hemoglobinopathies, hemolysis, and/or anemia.

It is to be understood that, in other certain embodiments of the methods/devices described herein, one or more other molecules, or fragments thereof, such as other glycated proteins, can be accurately tested. Since the present method facilitates detection and measurement of glycated blood proteins other than hemoglobin or site-specific HbA1c, the method is also useful for other technologies for the evaluation of glycemic control.

In certain embodiments, a targeted historic time record of glycated proteins from a period of about a few days up to about six weeks can be achieved depending on the specific glycated protein evaluated because different glycated proteins have different half-lives in blood. In contrast, prior tests are limited to assessing only one fixed time period.

This method and the platform using such method are highly miniaturized and are useful in a handheld device to provide real-time detection and analysis.

The method has the requisite sensitivity to be useful in medical testing of analytes.

The method further allows for the assessment of different types of proteins, such as glycated hemoglobin and other glycated forms of blood proteins.

In one method described herein, surface plasmon resonance is used with a highly functionalized aptamer sensing surface in order to provide an accurate, rapid and a relatively inexpensive method to assess glycemic compliance by measuring the levels of certain glycemic proteins in blood serum.

Determination of Aptamers

The method described herein is useful to detect different types of aptamers. In one embodiment, in order to isolate and identify oligonucleotides (aptamers) specific to the hemoglobin, albumin, and IgM glycated/non-glycated proteins, a Systematic Evolution of Ligands by Exponential (SELEX) enrichment protocol can be used.

While the standard SELEX protocol allows for the screening of ligands that are particular to a given protein of interest, described herein is an improved SELEX method which identifies secondary aptamers that are capable of detecting and capturing both protein versions (i.e., glycated and non-glycated forms), as further explained herein.

In one embodiment described herein, the identification of the secondary aptamer is used to determine the percent glycation which can be correlated to mean glucose levels for a given time frame.

Detection Platform: Protein Sensing and Surface Plasmon Resonance (SPR) Spectroscopy For protein detection, self-assembled monolayers (SAMs) are used to attach specific aptamers to gold SPR sensing surfaces. SPR spectroscopy itself is related to a phenomenon that occurs at the interface between conductors and dielectrics. At this interface, surface plasmons can exist which are charge density oscillations in the electron structure. These surface plasmons are most commonly excited with light in the visible to near-infrared spectrum. This excitation can occur either as freely propagating surface plasmons in a continuous metal surface or as a localized effect through the use of metal based nanoparticle structures. In one embodiment described herein, a freely propagating surface plasmon approach is used.

Briefly, valence electrons are disassociated from the atomic core, and in essence behave as an electron gas in the presence of an external electric field; it can be shown the surface plasmon is a bound wave with a corresponding wave vector equal to:

$$k_{sp} = \frac{2\pi}{\lambda} \sqrt{\frac{\epsilon_{metal} \epsilon_{sample}}{\epsilon_{metal} + \epsilon_{sample}}}, \quad (1)$$

where $\lambda$ is the wavelength of light, and $\epsilon_{metal}$ and $\epsilon_{sample}$ are the relative permittivity constants of media, respectively. Therefore, energy transfer to the surface plasmon will occur (i.e., it will be excited) if the incident light has an electric field vector with a transverse mode polarization component with an energy close to $k_{sp}$.

Figure 7:
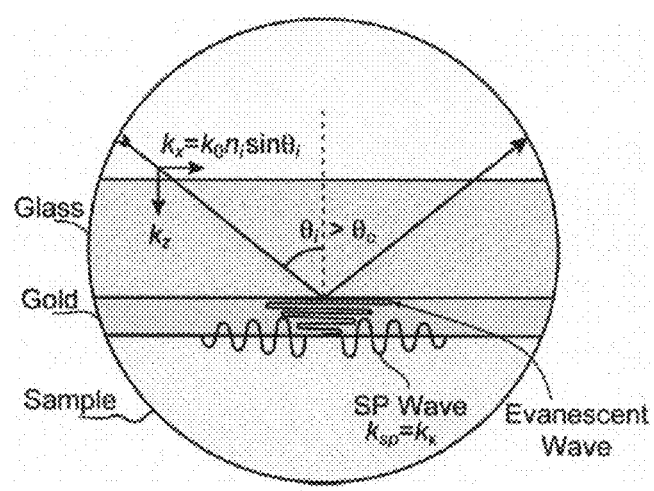
FIG. 7: Schematic illustration of an excited surface plasmon.

As shown in FIG. 7, the incident light vector has a component, $k_x$, which can be represented by the equation:

$$k_x = \frac{2\pi}{\lambda} n_i \sin\theta_i, \quad (2)$$

where $n_i$ is the index of refraction of the incident medium and $\theta_i$ is the incident angle of the incoming light contacting the metal surface. Surface plasmon resonance is highly sensitive to local variations in the refractive index of the sample due to the dependence of $\epsilon_{metal}$ and $\epsilon_{sample}$ to the wavelength $\lambda$ of the incident light. Changes in the refractive index can be measured using a reflectance based approach. The light reflected at the interface of two dielectric media, as shown in FIG. 7, generates an evanescent field with maximum intensity at the surface which will resonate with free electrons (i.e. surface plasmons). This results in light energy being transferred to the surface plasmon with a corresponding reduction in the degree of reflected light. The angle at which this decrease occurs is commonly called the resonance angle.

Figure 8A:
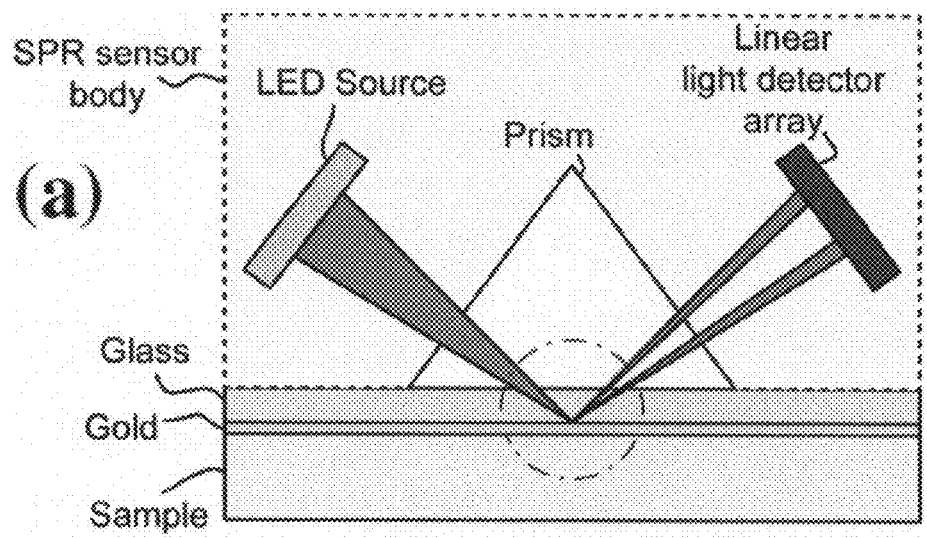
FIG. 8a: Schematic illustration of SPR with Kretschmann configuration.
Figure 8B:
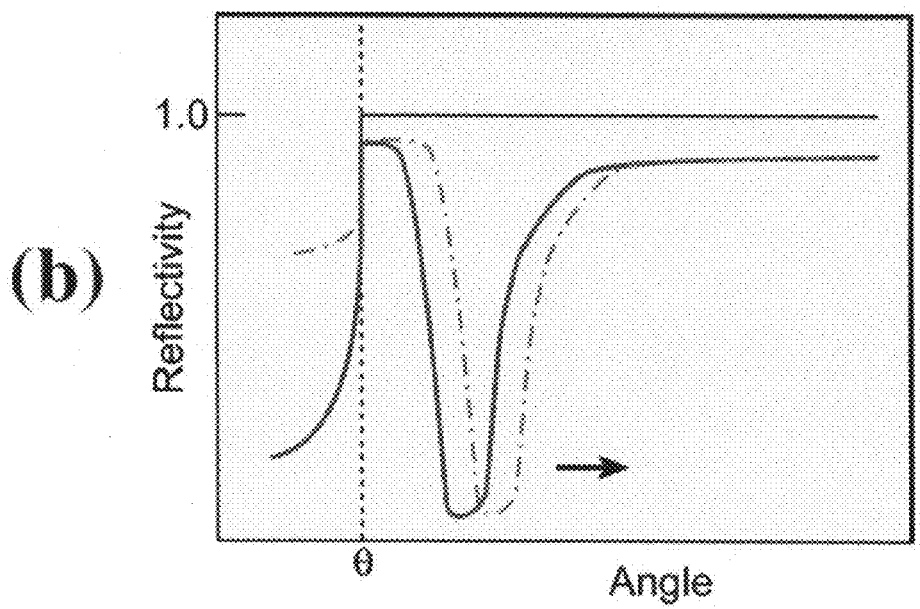
FIG. 8b: Schematic illustration of shift in resonance angle due to change in refractive index.

A Kretschmann instrumentation configuration used to measure the resonance angle is illustrated in FIG. 8a. In this configuration, light passes through a prism which is reflected at the glass-metal interface. An expanded version of the interaction at the metal-light interface is shown in FIG. 7. Any change in the refractive index at the metal/sample interface will result in a corresponding change or shift in the resonance angle, as illustrated in FIG. 8b.

The present method overcomes the drawbacks of use of SPR by itself, which is often adversely affected by the issue of lack-of-specificity. In addition, in the use of SPR by itself, if the sensing analyte does not elicit at least a moderate change in refractive index, the SPR also is also adversely affected by lack-of-sensitivity issues, as well.

The present method overcomes these adverse issues by using the selective aptamers described herein, and by using self-assembled monolayers (SAMs) with SPR. The present method provides such advantages as high sensitivity and selectivity, cost effectiveness, chemical and thermal stability, facile synthesis and storage.

Figure 9:
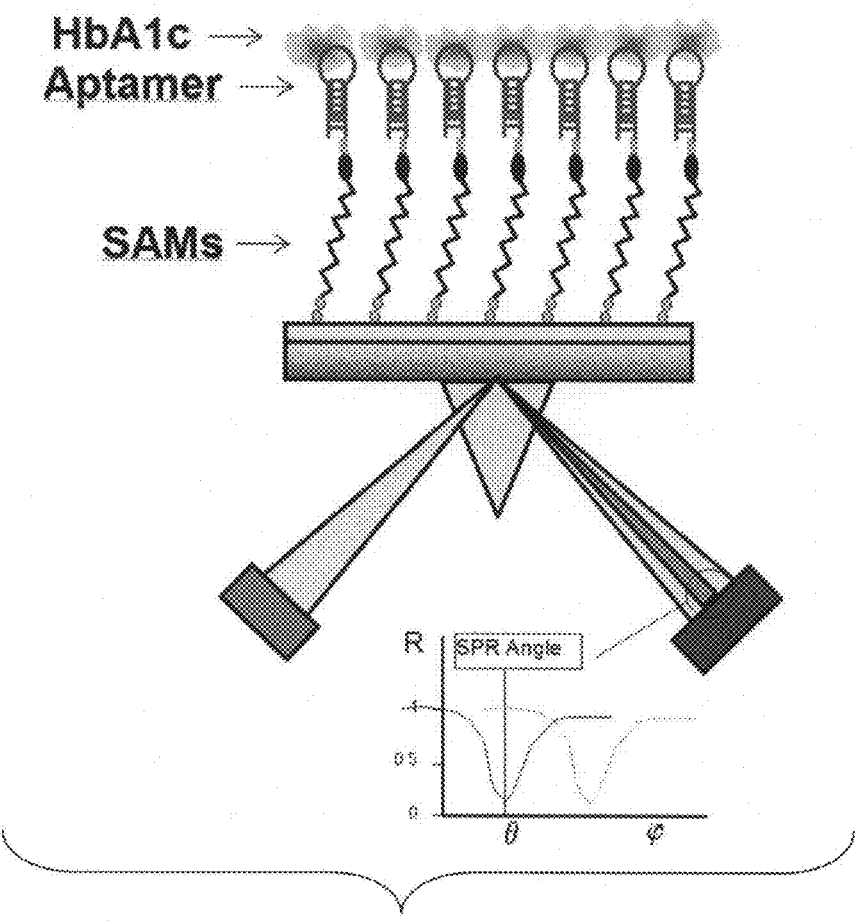
FIG. 9: Schematic illustration of binding HbA1c with aptamer immobilized on a SAM surface attached to a SPR sensing surface (top); and, schematic illustration of shift in resonance angle due to change in refractive index (bottom).

The presently described aptamer based sensing method is especially useful as a sensing element in biosensor applications. The nucleic acid nature of aptamers also renders the immobilization and regeneration easier. In one embodiment of an SPR application, the receptors (i.e., aptamers) are immobilized on solid substrates of various types for capturing target analytes or molecules (see FIG. 9).

In addition, the presently described method and apparatus overcome past problems with nonspecific adsorption of proteins that had been associated with SAMs where such nonspecific adsorption was detrimental to the sensor activity. In particular, the non-specific adsorption from complex sample matrices, like blood, urine or other clinical samples, was a major factor that limited the sensitivity.

Other limiting factors were the biophysical and chemical properties of the adsorbed surface itself. In such SAMs, these properties needed to be suppressed so as to ensure specific affinity interaction with the analyte of interest. Furthermore, proteins adsorbed on a SAM surface, partially lose their bioactivity due to conformational changes in secondary structure and/or non-optimal orientation and distribution on the surface. Also the protocols for preparation of surfaces and the conditions of mass transport significantly influence the protein adsorption response. Therefore, quantitative comparison of data obtained from different laboratories was difficult, and often inaccurate.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

Example 1

Materials

The identified aptamers were synthesized by Integrated DNA Technologies (Coralville, Iowa), including a 15 bp aptamer (APT1): 5'-NH$_2$—(CH$_2$)$_6$-GGTTGGTGTGGT-TGG-3' [SEQ ID NO:1], and a 34 bp aptamer (APT2): 5'-NH$_2$—(CH$_2$)$_6$-CTATCAGTCCGTGGTAGGGCAGGT-TGGGGTGACT-3'. [SEQ ID NO:2].

Tosylactivated magnetic beads (MBs) were purchased from Invitrogen (Carlsbad, Calif.). All other chemicals were purchased from Sigma Aldrich (Carlsbad, Calif.) at the highest purity available. Aptamer solutions were prepared with 1M pH 8 phosphate buffer. The 3-mercaptopropionic acid (MPA) solution was prepared in ethanol. Protein sample solutions were prepared using a 0.1M pH 7.2 PBS buffer solution with 5 mM KCl and 1 mM MgCl$_2$. The phosphoric acid (PPA) used was 100 mM. All other solutions were prepared in deionized (DI) water.

Instrumentation

SPR measurements were performed using a commercial grade SensiQ Discovery system (ICx Technologies, Arlington, Va.) at 25° C. This sensor is based on a Kretschmann configuration, in which the light from a light-emitting diode (LED) integrated with a prism is firstly polarized and then internally reflected from a gold surface. The angle of light reflection and the relative intensity was measured with a photodiode array. When the sample solution was applied to the sensing surface, the SPR profile minimum (also known as the SPR angle) shifted as a function of the refractive index of the loaded sample, giving a real time refractive index reading (although, by itself the sensor is not specific/selective for any given target). The SPR response profile was recorded by the SensiQ software and then processed within MATLAB®.

Electrochemical impedance spectroscopy (EIS) measurements were carried out using a Gamry Reference 600 potentiostat (Warminster, Pa.) in 5 mM $Fe(CN)_6^{3-}/Fe(CN)_6^{4-}$ solution with KCl as a supporting electrolyte. All the experiments were carried out at room temperature with the solutions purged with nitrogen gas for 15 minutes and the nitrogen blanket was maintained during the experiments. The experiments were performed at 25° C. Impedance spectra were collected in the frequency range from 0.1 Hz to 100 kHz with a potential amplitude of 5 mVrms at 10 points per decade. EIS results were analyzed by fitting the experimental impedance data to electrical equivalent circuit models. Parameters of the electrical-equivalent circuits were obtained by fitting the impedance function to the measured Bode and Nyquist plots with a complex nonlinear least square (CNLS) program built into the Gamry EIS 300 electrochemical impedance spectroscope.

Aptamer binding capacity was determined as follows: 10 nmol of amine modified aptamer was coupled to 10 mg washed magnetic beads (MBs) in a shaker incubator at 37° C. for 18 hours. The unoccupied binding sites were blocked by Bovine Serum Albumin (BSA). The aptamers-coupled MBs were washed thoroughly, and then 10 nmol of thrombin was mixed with the aptamer-coupled MBs for 2 hours in a shaker at room temperature. The control group was prepared by exactly the same method except for the absence of aptamers. The total and unbounded proteins were measured with a carboxyl functionalized SPR sensor provided by SensiQ.

To demonstrate the use an aptamer-based SPR sensor for detecting blood proteins, thrombin and antithrombin aptamer were chosen. Gold slides were prepared by physical vapor deposition (PVD) forming a 1 nm layer of titanium and a 50 nm layer of gold onto pre-cleaned microscope cover slides. These were then washed by copious amounts of DI water and ethanol. They were dried in nitrogen gas before usage.

To functionalize the gold slides, they were immersed in the 10 mM MPA solution for 30 min and then washed with ethanol and DI water. After the slides were dried, then they were immersed in a solution of N-hydroxysuccinimide (NHS) and N-(3-dimethylamnopropyl)-N-ethylcarbodiimide hydrochloride (EDC) (NHS 0.2M, EDC 0.05M) for 30 min. The slides were then washed with DI water and then immersed in the 5 µM aptamer solution. Finally, the slides were rinsed with the PBS buffer to flush off non-specifically adsorbed proteins. Then the slides were ready for measurement. In certain embodiments, this two-step surface functionalization process is applicable not only in SPR, but also Raman and fluorescence spectroscopy. The surface functionalization process is schematically illustrated in FIG. 1.

Non-coated (i.e., no gold) SensiQ base sensors were custom modified with the developed gold based SPR sensing surfaces. Specifically, freshly prepared aptamer-immobilized gold substrates were coupled to the stripped sensors with index matching optical oil. This was followed by then loading of 100 µL 1 M ethanolamine (EA) at a flow rate of 20 µL/min to block the non-occupied MPA sites activated by the EDC/NHS, followed by an injection of 100 µL of 100 mM phosphoric acid (PPA) at 50 µL/min to remove the non-specific binding. The running buffer was 0.1 M pH 7.2 PBS. The sensor was first normalized with the buffer for 10 min, then the thrombin sample (25 µL) at concentrations of 5 nM, 25 nM, 50 nM, 250 nM 500 nM, 1000 nM, 2000 nM were loaded at 5 µL/min. Samples with BSA were all prepared with 400 nM BSA. All data was recorded at 290 s, 300 s, and 310 s after the sample injection and averaged. Sensor regeneration was performed by the injection of 100 µL PPA at 50 µL/min followed by washing with the running buffer.

Results for Example 1

EIS Measurement

Figure 2:
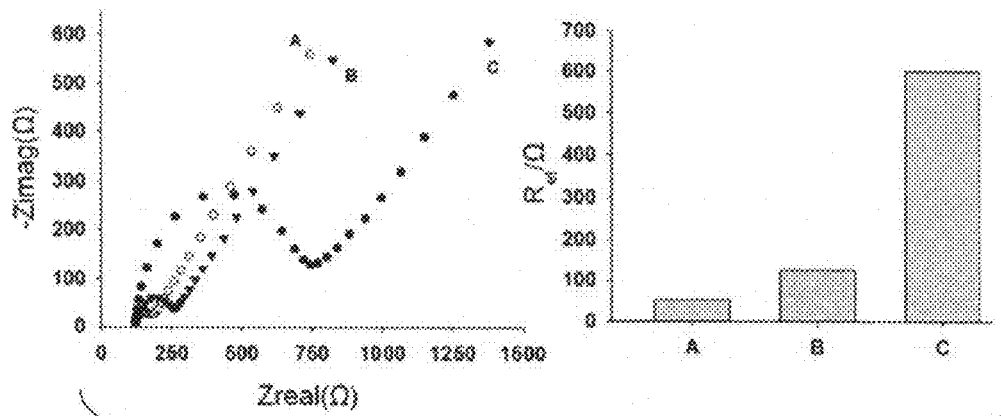
FIG. 2: Nyquist plots of impedance spectra obtained in 100 mM PB solution (pH 7.2) containing 5 mM $Fe(CN)_6^{3-}$/Fe $(CN)_6^{4-}$ (Column A) Bare Au; (Column B) Au/MPA/EDC-NHS/EA/PPA; (Column C) Au/MPA/EDC-NHS/EA/PPA/APT 1. The right plot shows the ($R_{et}$) of each layer. Impedance spectra were collected in the frequency range from 0.1 Hz to 100 kHz with a potential amplitude of 5 mV rms at 10 points per decade.

The successful immobilization of each functionalized layer was confirmed through EIS measurements. FIG. 2 shows the Nyquist plots of impedance spectra at different electrodes. The bare gold electrode represented a very small circle at high frequencies, indicating a very low electron transfer resistance to the redox probe dissolved in the electrolyte solution (curve A). When the MPA was immobilized on the electrode and treated with EA and PPA, the electron transfer resistance ($R_{et}$) increased to 125Ω, (curve B). Then, when 5 µM of the APT1 aptamer was added and bound with the SAM, $R_{et}$ increased to 600Ω (curve C). In this embodiment, the reactive sites on the gold electrode were blocked by EA (ethanolamine) to prevent non-specific adsorption of aptamers onto the gold surface, thus ensuring that the aptamers were attached only to the SAM. The $R_{et}$ increase is caused by the electrostatic repulsion between the immobilized aptamer and the redox probe, causing a barrier for the interfacial electron transfer. These results show successful immobilization of the SAM layer onto the gold surface and stable bonding of the aptamer to the SAM Magnetic Bead (MB)—Based Maximum Binding Capacity After the aptamers-coupled MBs were thoroughly washed, thrombin was added and the concentration change was measured using a carboxyl modified SPR sensor. The refractive index is controlled only by the concentration change of the added thrombin. Other experimental variables such as protein degeneration and temperature had minor influences on SPR results and thus were not considered to affect the results.

Figure 3:
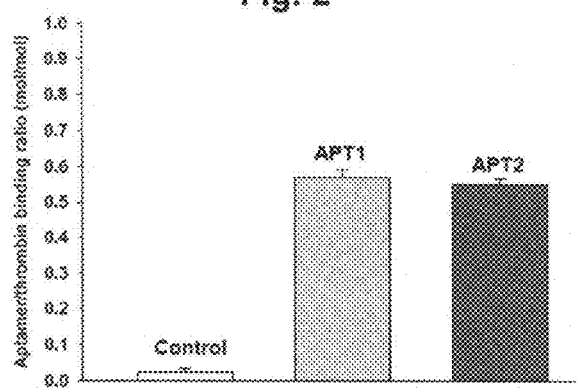
FIG. 3: Graph showing aptamer/thrombin binding ratio in mol by the magnetic beads coupling method.

As shown in FIG. 3, the concentration change of thrombin was insignificant for the control group (less than 3%) which was not functionalized by the aptamer. This shows that the concentration change in the two experimental groups was mainly due to the binding between the aptamer and thrombin. For the APT1 and APT2 groups, the mixture of aptamer functionalized MBs and thrombin solution was allowed to react for 18 hours and the reaction was considered to be completed based on the MB manufacturer's specifications. Thus, the final concentration reflected the maximum mol/mol binding capacity of aptamer to thrombin.

The results showed the binding ratio of APT1 (57.1%) has a better capacity than APT2 (55.2%). Both aptamers had more than 50% mol/mol binding ratio to thrombin, indicating that they are good receptor candidates for thrombin sensing applications. It is to be understood that, in certain embodiments, not all the aptamers may bind to the MBs and therefore the actual binding capacity of the binding aptamers toward target compound/s may be slightly greater.

The Control group was comprised of MBs without aptamer functionalization and all binding sites blocked by BSA. The aptamers-containing groups were: APT1- and APT2-MBs functionalized by the respective aptamers with the unoccupied binding sites blocked by BSA. The error bars represent the standard deviation of the values determined from three samples.

SPR Results

Figure 4:
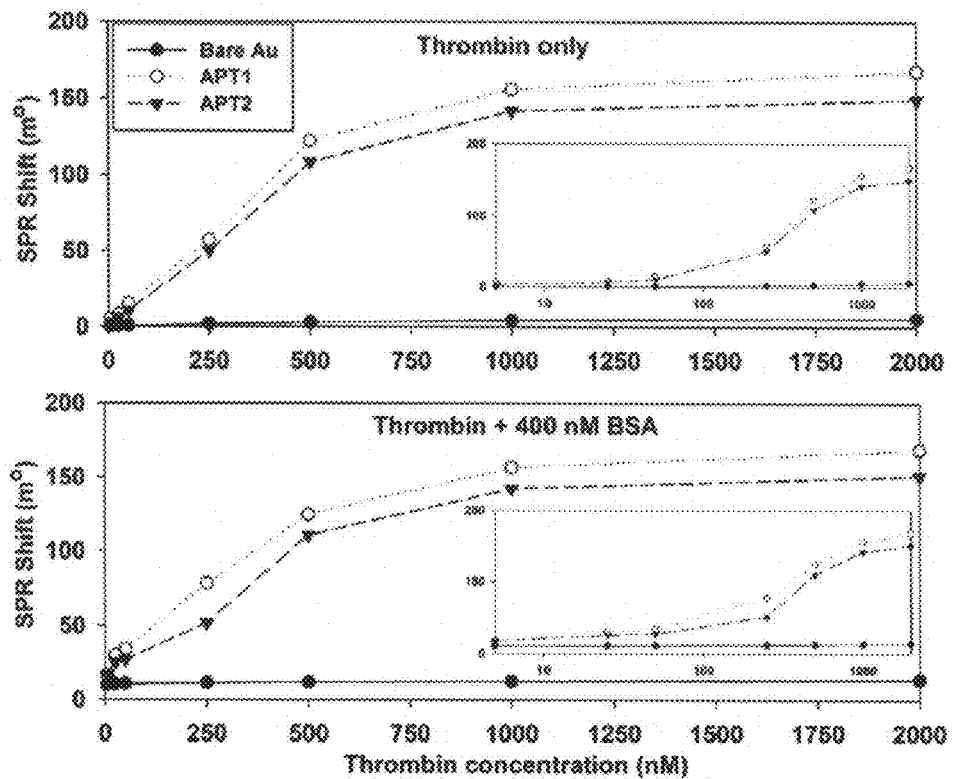
FIG. 4: Graphs showing SPR response of bare Au and aptamer-modified sensors. All data points were averaged from 3 experimental data readings. Samples were thrombin only (top plot) and thrombin with 400 nM BSA (bottom plot). The inlay plots are same data plotted on logarithmic scale to allow for better visualization at lower concentrations.

Two different aptamers were immobilized on gold surfaces and the binding performance of each one was compared. For reference, samples of different thrombin concentrations (5 nM, 25 nM, 50 nM, 250 nM, 1000 nM, 2000 nM) were individually loaded onto a bare Au sensor, an APT1 sensor and APT2 sensor, respectively. A secondary experiment was then performed using the same thrombin concentrations; however, with a 400 nM BSA confounding component added to each thrombin sample for comparison. As shown for the "Thrombin only" experiment in FIG. 4, the SPR shifts were very low for the bare Au sensor surface even for the relatively high thrombin concentrations.

In contrast, for the aptamers-modified sensors the SPR shifts were significantly enhanced and the optimal detection range was 5 nM to 1000 nM (linear range). The "Thrombin+ 400 nM BSA" data (shown in FIG. 4) shows where a large 400 nM BSA confounding concentration component was added to each thrombin sample concentration. As compared to the thrombin only group, the responses are nearly identical, indicating the aptamers-modified APT1 and APT2 sensors are highly specific to only thrombin.

Figure 5:
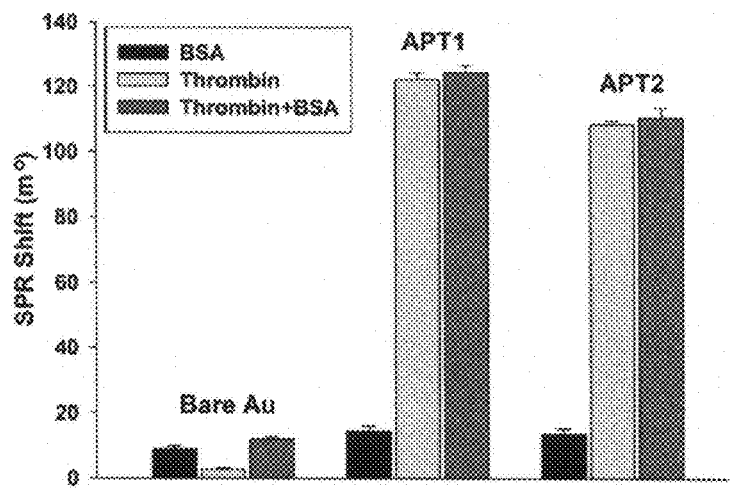
FIG. 5: Graph showing SPR responses of different sensing surfaces for 400 nM BSA (BSA group), 500 nM thrombin (Thrombin group), and 500 nM thrombin with 400 nM BSA (Thrombin+BSA group). The error bars represent the standard deviation of the values determined from three freshly prepared samples.

This is further illustrated in FIG. 5, which shows the SPR shift for the 500 nM thrombin concentration with, and without, 400 nM of BSA. Adding BSA to the sample had minimal effect on the SPR response for the aptamer modified sensors, indicating a good selectivity of the sensor toward thrombin. This is in contrast to the bare Au sensor, which experienced a significant change between the thrombin samples with, and without, BSA. The APT1 modified sensor did have a slightly higher shift than the APT2 sensor for all the thrombin concentrations. The slope of the fitting line for APT1 is also slightly larger than APT2 in the linear response range (FIG. 6), again demonstrating a better sensitivity. These two aptamers bind to different sites of thrombin, thus the affinity to the target is different in both the interfacial binding environment and in solution.

Antibody Sensing

In the MBs binding tests, the APT1 had a slightly higher binding capacity than APT2, which corresponds to the SPR results in terms of sensitivity of the functionalized sensor. While not wishing to be bound by theory, it is believed that in this embodiment, this may be due to the smaller aptamer having a greater probability to access the binding sites of the target protein. Also, in certain embodiments, larger aptamers that have more complicated secondary structures may require an extra spatial flexibility to form bonding with target compounds.

As Example 1 herein shows, the MPA layer has excellent coverage rate on gold and is useful for antibody immunization for biosensing purposes. These results also show that the amine-modified aptamer is readily immobilized onto the MPA layer and the sensor performance was comparable to antibody-based sensors.

Three sensing slides were prepared for each aptamer and also the control group. The sensor to sensor performance was consistent when using the freshly prepared samples, yielding relatively small errors for each measurement and averaging less than 2% standard deviation of the total signal (error bar showed in FIG. 5).

Adding BSA did introduce a slightly larger error and by lowering the flow rate and increasing the sample loading time, the error can be reduced although deemed not significant enough to be considered. The majority of the error is thought to be caused by temperature variance; as such, in some embodiments, placing the sensor in a temperature controlled environment can help increase the accuracy.

The sensing surface described herein had an optimal dynamic range from 5 nM to 1000 nM, which is comparable to or greater than the largest reported dynamic ranges for thrombin aptamer-based sensing techniques. Since the thrombin concentration range in the human blood is reported to be within the low nanomolar to low micromolar range, the presently described method is well suited for in vivo thrombin quantitative detection.

Reversibility of Sensors

Figure 6:
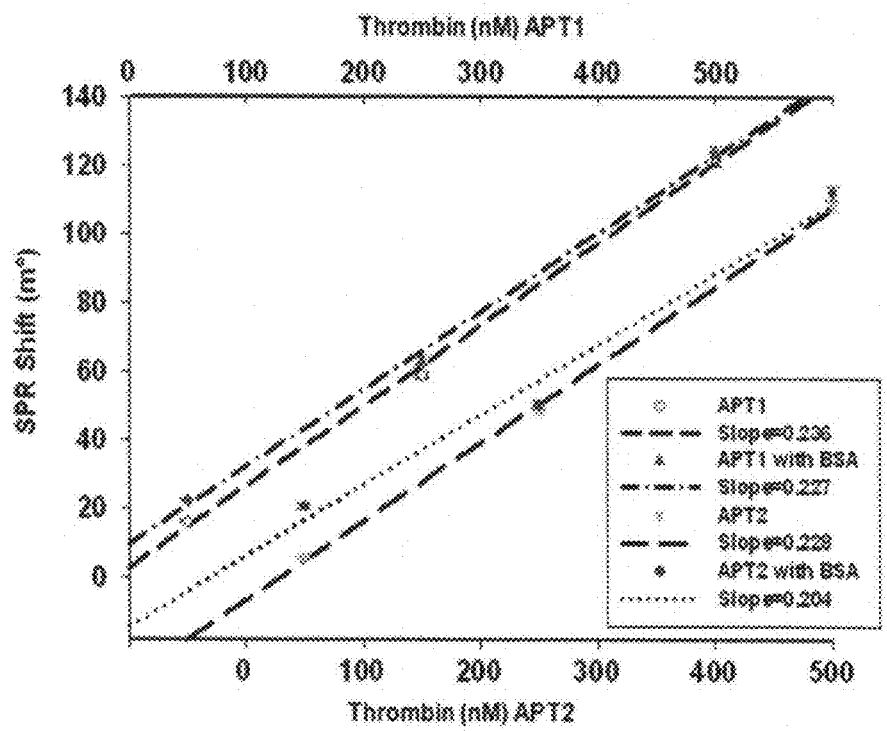
FIG. 6: Graph showing SPR responses of different sensing surfaces for 50 nM, 250 nM, 500 nM thrombin with and without 400 nM BSA, upper axis (APT1), lower axis (APT2); the zero position of lower axis has been shifted intentionally to better distinguish between data points that would be overlapping.

To test the reversibility of the sensor, fixed sample concentrations were repeatedly loaded to the sensor 10 times. The sensor regeneration was done by PPA. The average SPR response with error bars for standard deviation using thrombin concentrations of 50 nM, 250 nM and 500 nM are shown in FIG. 6. All data were obtained from freshly prepared sensing slides. The SPR response generally decreased about 0.5% for each loading for a same sample concentration. All the sensing slides maintained more than 95% of the original SPR shift response after the $10^{th}$ loading. Also, the second sample loading usually had the greatest response change as compared to the following loadings. With a longer PPA injection time, the sensor recovery rate can be increased, depending on the experimental requirements. The appearance of BSA did lower the sensitivity of the sensor (e.g., in FIG. 6, the appearance of BSA did reduce the slope slightly in the response curve), although it did not affect the reversibility of the sensor. FIG. 6 also demonstrates that sensor maintained a linear response with and without the appearance of BSA in the 50 nM to 500 nM sample range.

Example 2

Other Embodiments of Sensors

In another embodiment, the sensor can include a mixed length spacer layer. In one non-limiting example, the mixed length layer can be as 11-mercaptoundecanoic acid (MUA) combined with MPA, which can be used in certain embodiments to increase the sensitivity and specificity.

In other embodiments, a mixed length spacer can be included to help form and maintain the specific shape of the immobilized aptamers.

In another embodiment, a hydrophilic group such as ethylene oxide can be inserted onto the $5^c$-end of the aptamer in order to reduce nonspecific protein binding.

In certain embodiments of the two step immobilization method described herein, spacing the aptamers can also done by adjusting the MPA SAM density, or by co-incubating ethanolamine and the aptamer at various molar ratios.

Detection of Blood Proteins

For the detection of different blood proteins, in order to find the aptamer that specifically and directly binds to the target protein of interest, a SELEX procedure can be used. Then, the developed aptamer can then be amine-terminated and immobilized onto the gold surface using one of the presently described methods in order to form a target specific sensor for almost any protein. As such, aptamers can be generated through SELEX to target specific compounds with advantages over antibodies.

The two-step immobilization method described herein is especially useful for the immobilization of a SAM and amine-terminated aptamer onto a gold SPR sensing surface. The presently described SPR sensor provides advantages, such as low sample consumption, the lack of labeling requirement, high sensitivity, and fast response time. Additional advantages of the two-step immobilization method include demonstrable cost efficiency, good reversibility, uniform density, and use as a robust and specific blood protein detection platform.

Example 3

SPR Aptamer Based Glycated Albumin Protein Sensing

Glycated human serum albumin (HSA) was both detected and quantified. The aptamer (thiolated, non-reduced) developed and used was 5'-SH—(CH$_2$)$_6$-CCGAAACCAGAC-CACCCCACCAAGGCCACTCGGTCGAAC-CGCCAACACTCACCCCA-3' [SEQ ID NO: 3].

Gold slides were prepared by physical vapor deposition (PVD) forming a 1 nm layer of titanium and a 50 nm layer of gold onto pre-cleaned microscope cover slides. The gold slides were then washed by copious amounts of DI water and ethanol. The gold slides were dried in nitrogen gas before usage.

The thiolated aptamer was diluted by 1M phosphate buffer pH 8 and mixed with Cleland's REDUCTACRYL™ reagent in a shaker for 2 hours to reduce the double thiol bond in the aptamer sequence. Cysteine is a water soluble thiol-containing amino acid that can directly bind to the gold surface to form a self-assembly monolayer (SAM), which was then added to the aptamer solution to help space out the aptamers, fill the gaps between aptamers, and reduce the non-specific surface absorbance. The final concentration of the aptamer in this preliminary experiment was set to be 1 µM and the aptamer:cysteine molar ratio was 1:10. The gold slides were immersed in the aptamer/cysteine mix solution at 37° C.

After the immobilization process, the gold slides were washed with 0.01 M PBS buffer pH 7.4. The functionalized surface was then coupled to the corresponding SPR sensor, and 1 µg/mL total protein HSA samples (i.e., total=glycated+nonglycated) were prepared for the given glycated percent (%) ratios (glycated/total protein): 2, 6, 10, 14, and 18%.

Figure 10:
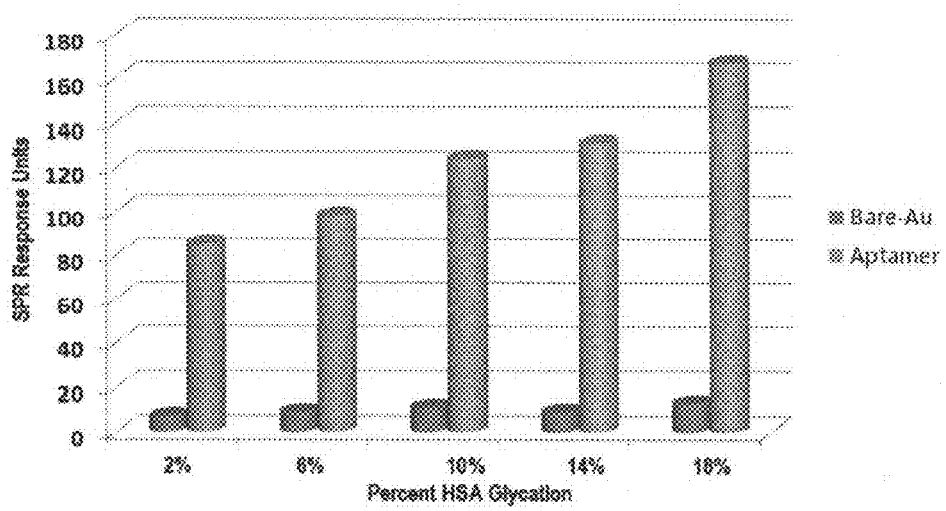
FIG. 10: Graphs showing SPR response for HSA at different glycation levels (% percent ratios; glycated/total protein). Note: the total protein concentration of each sample is constant at a level of 1 μg/mL total protein. (Green) Aptamer functionalized surface (Red) Bare-Au surface.

SPR responses were recorded for each respective sample. The results for the functionalized surfaces along with the bare-Au surfaces are summarized in FIG. 10. The aptamer functionalized SPR surface responds directly to changes in the glycated protein content. It is to be noted that the total protein concentration is constant at 1 µg/mL between samples.

The non-functionalized surface (i.e., bare gold) exhibits a negligible response, further illustrating the enhanced sensitivity in the functionalized surface. Although small in length (40-60 nt), in certain embodiments, aptamer sequences may differentiate targets based on size and charge, and affinity may be affected. While not wishing to be pound by theory, the inventors herein now believe that the 3D structure of the aptamers may also plays a role; one non-limiting examples include the cytosine-rich bulge-loop structure and the ACC (C) or (C)CCA motifs.

Aptamers for Non-Glycated and Glycated Protein Binding Sites for HbA1c, Albumin, and IgM Aptamers were developed to attach to the self assembled monolayers (SAMs). For certain embodiments, the proteins hemoglobin, albumin, and IgM are useful since half-life of each provides information that spans short, intermediate, and long term historical records in glycemic control. A summary of the properties for some common blood proteins are provided in Table 1 below.

TABLE 1

Related properties of blood proteins

| Target Protein | Half-life (weeks) | Average Concentration (mg/mL) | Percent Glycation (%) |
|---|---|---|---|
| Hemoglobin | 6-8 | 325 | 6-15 |
| IgG | 3-4 | 12 | 20 |
| Albumin | 3 | 33 | 16 |
| IgM | 1 | 1.4 | 15-35 |
| Fibrinogen | 0.5 | 2.5 | 6 |

Glycation of the respective proteins can be performed by incubation (37° C.) of the respective proteins in pH 7.4 PBS containing 1M glucose and DTPA for two days. The glycated proteins are then subjected to a dialysis process and then can be further enriched by affinity chromatography. In this step, the glycated proteins can be separated from the respective non-glycated forms using boronic acid immobilized on polyacrylamide beads in the support column. Through this process, both the nonbound and bound fractions can be collected and further concentrated using filtration methods.

To achieve isolation and identification of key oligonucleotides (aptamers) specific to hemoglobin, albumin, and IgM in both the glycated and nonglycated versions of the proteins, an improved Systematic Evolution of Ligands by Exponential (SELEX) enrichment method can be used, as further explained below, and schematically illustrated in FIG. 12.

The improved SELEX method allows for the screening of ligands that are particular to a protein of interest. The improved SELEX method can be conducted by generating a large library of randomized RNA sequences. This library usually contains $10^{14}$-$10^{15}$ different RNA species that fold into different structures depending on their particular sequence. This library is then incubated with the target protein of interest, and those RNAs contained in the library that bind the protein are then separated from those which do not. The retained RNAs are then amplified by RT-PCR and transcribed in vitro to generate a pool of RNAs that have been enriched for those that bind the target of interest. This selection and amplification process can be repeated between 8 to 12 rounds until the RNA ligands with the highest affinity to the target protein are isolated. These aptamers are then cloned and sequenced.

Determination of Ratio of Glycated Protein-to-Total Protein

The percent ratio of glycated protein to total protein measurement was related to average blood glucose over a given time window.

Aptamers specific to the glycation sites of the target proteins can be generated. Also, aptamers that will bind both the glycated and non-glycated versions of the respective proteins were generated. In one embodiment, glycated versions of hemoglobin, albumin, and IgM proteins were used as the target in the SELEX protocol. The resulting reduced aptamer pool contains both the non-glycation site and glycation-site specific aptamers. At this point and in a later round(s), non-glycated protein (i.e., normal protein) can then be introduced, in which, present aptamers that recognize the glycation site do not bind and can be recovered for characterization. This method provides separate aptamers that are capable of binding both the glycated/nonglycated versions of the proteins, as well as those that are only specific only to the glycated versions.

Optimization of Surface Plasmon Resonance Self Assembled Monolayer Aptamer-Based Functionalized Surface The identified aptamer can then be initially characterized for general performance including binding properties, sensitivity, specificity, and selectivity. Presented in Table 2 below are examples of target specifications based on performance levels.

TABLE 2

| Parameter | Specification Detection Limit |
| --- | --- |
| Hemoglobin | $10^{-7}$ mol |
| Albumin | $10^{-6}$-$10^{-5}$ mol |
| IgM | $10^{-8}$-$10^{-7}$ mol |
| Cross-Reactivity | <6% |
| Assay Time | <15 min |

In particular, one method for characterizing binding affinities is the use of a SPR method. Based on the aptamer candidates identified, SPR is useful to generate the respective binding response curves. For example, certain devices (such as SensiQ, iCx Nomatics) are equipped with a dual microfluidic channel and have controllable flow rates. The tests can be performed using immobilization methods similar to those described for FIG. 1.

Modifications to Facilitate Immobilization

Also, in certain embodiments, the glycated and non-glycated specific aptamer candidates can be modified with a 5'-$NH_2$—$C_6$ attachment to facilitate immobilization onto a —COOH modified gold SPR surface. SPR measurements are then used to characterize the respective affinity constants for the aptamer candidates.

In addition to the affinity tests, using the SPR chip immobilized aptamers, both the specificity and selectivity can be evaluated. In such embodiments, the respective aptamer chips were exposed to each target protein in both the glycated and non-glycated forms. Cross-reactivity between the two forms for a given protein, as well as, for different proteins (e.g., albumin for a HbA1c aptamer chip) was thus determined. In certain preferred embodiments, the target cross-reactivity is desired to be below about 6%. If it is determined that this criterion is not met, the SELEX protocol can be repeated with improved selection conditions (e.g., increasing the frequency of elimination rounds), in order to further improve cross-reactivity performance.

It is also understood that good target recognition can also be affected by the aptamer linking process used for immobilization. In certain embodiments, the method can include the use of one or more alternative linking methods of the aptamers. In certain embodiments, the linkages can be through 3'-amino, thiol, or other potential linkages.

It is also within the contemplated scope that such linkages can be modified by, for example, controlling certain parameters, such as the density and length. Thus, aptamers and linkage methods can be optimized to provide maximum desired performance. In addition, the method described herein to create the functionalized surfaces can be optimized to provide a desired level of uniformity in the surfaces, as well as to optimize the aptamers sensor response.

Self-Assemble Monolayer (SAM) Linkages

In addition to the linking methods described above, another method that can be used include linkage through a binary self-assembled monolayer (SAM) and reductive desorption process. Since SAMs' packing density and lengths of SAMs affect the SPR signal, the density and length of the binary SAMs can be controlled using a reductive desorption process.

In a particular embodiment, synthesized dithiobis-N-succinimidyl propionate (DTSP) can be used with (1-mercapto-11-undecyl)tri(ethylene glycol) (PEG3) for tailoring a mixed SAM. PEG3, which is resistant to protein adsorption, can be employed to prevent non-specific adsorption of proteins. In addition, the carboxylic group in DTSP will form a stable bonding with the aptamer.

In a particular embodiment, a thiol SAM immobilization method using dithiobis-N-succinimidyl propionate (DTSP) was used in a phosphate buffer solution. DTSP is useful for SAMs due, at least in part to its distinctive surface properties, such as hydrophilicity, wettability, chemical reactivity, and an affinity towards proteins such as hemoglobin and cytochrome c.

For the binary-SAM immobilization, 3-mercaptopropionic acid (MPA) and (1-mercapto-11-undecyl)tri(ethylene glycol) (PEG3) can be used. In certain embodiments, MPA is chosen because it has a lower redox potential than PEG3, which means MPA can be easily eliminated by reductive desorption leaving PEG3 intact. DTSP is able to form a covalent bond with the amino groups of the aptamer while PEG3 does not, so that the aptamer will attach to DTSP only.

Two-component thiol solutions can be prepared by mixing 1 mM ethanol solutions of MPA and PEG3 at various ratios, while keeping the total concentration of the binary SAMs at 1 mM. The binary SAM of MPA and PEG3, whose ratios are 20:80, 50:50 and 80:20, can then be formed on a gold electrode by soaking the electrodes into the mixed thiol solution for 1 hr.

Figures 11A, 11B, 11C, 11D, 11E:
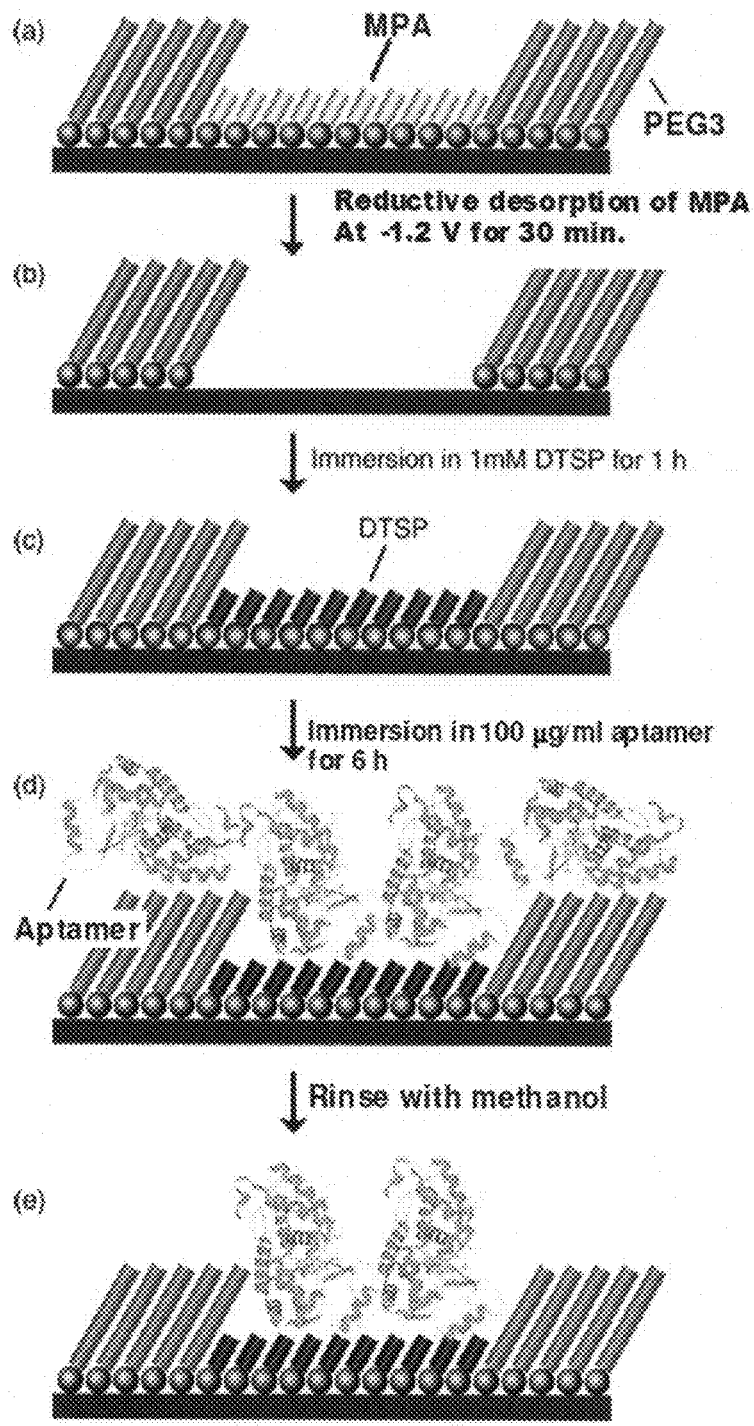
FIGS. 11a-11e: Schematic illustration of reductive desorption for DTSP-PEG3 binary SAM formation.

Referring now to the schematic illustration in FIGS. 11a-11e, a binary SAM formation and reductive desorption procedure is shown. First, the binary components of 3-mercaptopropionic acid (MPA) and PEG3 are adsorbed on the gold surface in an ethanol solution (FIG. 11a). The reductive desorption of MPA from the gold electrode is performed in 0.5 M KOH solution. The adsorbed MPA in a phase-separated binary SAMs of MPA and PEG3 is selectively reduced by applying the potential of −1.2 V for 30 min (FIG. 11b).

After reductive desorption of MPA, the sample with the PEG3 layer is immersed in the 1 mM DTSP solution to form DTSP layers (FIG. 11c). FIG. 11d shows aptamer immobilization, and FIG. 11e shows removing aptamer from PEG3.

The aptamer covalently couples to the SAM of DTSP exposing —COOH end groups. For covalent bond formation, aptamer (50 µg/ml) in PBS is injected together with freshly prepared NHS and EDC. Aptamers having amino groups at the N-terminals and can be immobilized on the DTSP SAM through CO—NH amide bond formation. The ratio of DTSP and PEG3 will be varied to control the packing of the SAMs and as result, the binding of the protein that gives the optimum SPR signal can then be obtained.

Measurement of Surface Coverage

Cyclic voltammetry (CV) and electrochemical impedance spectroscopy (EIS) can be used to measure the surface coverage of immobilized SAMs and redox responses of the samples. The surface composition can be estimated from the peak areas of a cyclic voltammogram for the adsorbed thiols. Responses of the binary SAMs deposited on the modified electrode can be compared with those of the unmodified electrode.

Cyclic voltammogram of the reductive desorption can be recorded in 0.5 mol $dm^{-3}$ phosphate buffer solution using a Ag—AgCl-saturated KCl electrode as the reference electrode and a platinum wire as the counter electrode. The CV curves of SAMs+Aptamer coated gold electrode (Au+SAM+ aptamer) and reductive eliminated SAMs and aptamer on the gold electrode (Au+RD SAM+aptamer) can thus be compared. The CV curves can be recorded at the scan rate of 100 mV/s for the reductive elimination. In each voltammogram, a down peak of reductive desorption of SAM is expected to appear around 50 mV.

Both the length and density of the SAM can be controlled to obtain the optimal SPR response. When the linker length is long, more aptamers can be immobilized, but the SPR dip may get broader as the aptamers are farther away from the surface. Likewise, when the linker density is high, more aptamers can be attached to the SAM, but then the SPR dip may get narrower and more difficult to detect. These aptamer modified surfaces can be characterized by the methods used with the 5'-$NH_2$—$C_6$/—COOH method.

Calibration and Validation of the Developed Functionalized SPR Sensing Surfaces

The SPR sensing platforms for HbA1c, albumin, and IgM glycated/non-glycated protein detection can initially be calibrated in tests using a saline buffer with known target proteins ratios. Respective sample solutions can be prepared for fixed levels of total protein at reasonable ratio levels compared to those seen in blood (see Table 1).

For each sample, the ratio of glycated protein to the total amount of protein can be varied over a desired range (e.g., for HbA1c % levels between 6 to 15% correspond to average glycemic levels of 60 to 360 mg/dL, respectively). In such embodiment, a range from 1 to 25% v/v would be appropriate. The SPR response in the respective samples can then be evaluated and a calibration model can be determined in relation to % glycation and the standard error of calibration can be calculated. To further assess the accuracy of the developed SPR assays, independent samples (i.e., those not used in calibration) can be used to assess assay performance based on the respective calibration model(s). Both relative and absolute errors can be determined and compared with the ranges that would be required for useful diagnostic purposes.

Testing of Serum Blood

To assess performance in actual blood serum, blood serum from a non-diabetic source can be utilized. The serum samples can be analyzed to determine the respective fractions of glycated versus total protein (for both protein targets) through standard clinical testing.

Using these values as references, individual samples can be doped with specific amounts of the respective glycated protein(s). Testing evaluation similar to that utilized with the saline tests can be repeated. It is understood that, due to high concentrations of certain target proteins in serum (e.g., hemoglobin as shown in Table 1), it may be desired to dilute the samples prior to running the tests. In addition, other potential confounding effects such as introducing variations in sample composition, outside that of glycated protein, can be tested as issues may arise due to the complex chemical composition of serum.

Example 4

Improved SELEX Method for Aptamer Identification Targeted to Glycated and/or Non-Glycated Protein Sites The SELEX protocol was improved in order to allow for the identification of aptamers with an affinity to glycated protein sites. This improved SELEX protocol allowed for the determination of the percent ratio of glycated protein to total protein.

Aptamers specific to the glycation sites of the target protein(s), in addition to those that will bind to both the glycated and non-glycated versions of the respective proteins, were generated. In order to generate such aptamers for a respective protein (e.g., hemoglobin, albumin, IgM, etc. . . . ), in a first round of amplification, the SELEX protocol was applied to a glycated version of the respective proteins. This first round of the SELEX protocol resulted in a reduced aptamer pool that contained both "non-glycation-site-specific" aptamers and "glycation-site specific" aptamers.

A non-glycated protein (i.e., normal protein) is introduced into the pool obtained in the first round SELEX amplification process. In at least a second round of amplification, the aptamers in the pool that bind to such non-glycated protein are not eluted in this specific SELEX round, and are, therefore, are removed from the pool. This improved SELEX protocol improves the chance that aptamers specific to the glycated sites will remain in the ongoing pool. Such remaining aptamers can then be recovered for characterization in subsequent SELEX rounds as part of a standard SELEX process. It is to be understood that, in other embodiments, the uses of "glycated" protein and "non-glycated" protein can be reversed; e.g., where a "glycated" protein is introduced onto the pool obtained in the first round SELEX amplification process.

Determination of High Affinity Glycated and/or Non-Glycated Protein Aptamers

A protein molecule (e.g. albumin) has multiple sites available for glycation. The glycation level usually refers to the percentage of a given protein concentration that has been glycated with respect to the total protein level, whereas, the glycation rate refers to how many sites within a single protein molecule has bound glucose or glucose derivatives. The 3D conformation and the charge distribution are significantly different between a highly glycated and non-glycated protein molecule, but very similar between a lightly glycated protein molecule (i.e., single glycation point) and non-glycated protein molecule. Therefore, the development of a high affinity single-site specific glycated protein binding aptamer that has a low affinity to the non-glycated form is very challenging.

Figure 12:
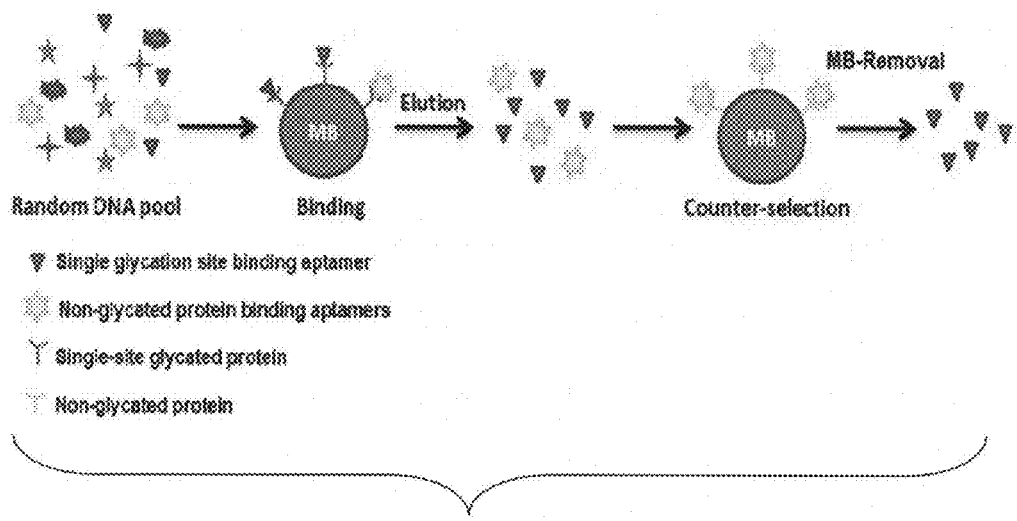
FIG. 12: Schematic illustration of a MB counter-selection for a SELEX process.

One example of the improved SELEX in vitro selection protocol is shown in FIG. 12, where a large random DNA pool is initially mixed with a glycated protein target immobilized onto magnetic beads (MBs); that is, a primary or "glycated-protein-target-MB" complex.

Aptamers with high affinities to the glycated protein target will bind and form an "aptamer-glycated-protein-target-MB complex."

The "aptamer-glycated-protein-target-MB" complex is separated out from the initial DNA pool.

In a subsequent step, the bound aptamers are eluted from the "glycated-protein-target-MB" complex (i.e., the single or lightly glycated form of the protein).

At this point, a control protein (i.e., a non-glycated form of the protein), which is coupled to a second set of MBs (a secondary or "non-glycated-protein-target-MB" complex) is added to this first elution.

The "non-glycated-protein-target-MB" complex is used to remove "selective" aptamers in the first elution that also have an affinity to the non-glycated protein form.

In a subsequent step, the "selective" aptamers are eluted from the "non-glycated-protein-target-MB" complex.

Upon the removal of the "non-glycated-protein-target-MB" complexes via, the remaining "selective" aptamers are those aptamers that have a high affinity to the single or targeted glycation sites.

At this point, a standard SELEX method can be used to amplify these remaining "selective" aptamers that have a very high affinity to the desired glycated protein site.

Specifically, this improved SELEX method allows for the development of high affinity single glycation site aptamers that have a low affinity to the non-glycated form of the protein. This improved SELEX method is also useful to generate aptamers that have an ability to distinguish analytes/molecules that have very similar chemical structures.

Examples of Glycated and Non-Glycated Aptamers

Examples of useful aptamers are shown below, where XXX and YYY refer to any one or more of additional binding groups such as biotin, thiol, amine, etc. that may be used to facilitate development of a given self-assembly-monolayer (SAM).

```
Glycated Hemoglobin Aptamers
                                         [SEQ ID NO: 4]
5'-XXX-ATCCTTCATCCCATGGTTGCATATTGATTGCCGGTTCCTTAAA
T-YYY-3';
and

[SEQ ID NO: 5]
5'-XXX-AGGGAAAGGTGTGGGTTAGGAGCTTGAAATCGAAAGAGGGGC
G-YYY-3'.

Non-Glycated Hemoglobin Aptamers
                                         [SEQ ID NO: 6]
5'-XXX-TTAGCGAGCTGCACACACAATGGACTCGTCATACCGTGCTGTT
T-YYY-3';
and

[SEQ ID NO: 7]
5'-XXX-ATCTGCAGAATTCGCCCTTGCTGGTGCAGTACACACCCGGCGG
G-YYY-3'.

Glycated: Human Serum Albumin (HSA) Aptamers
                                         [SEQ ID NO: 8]
5'-XXX-CTCACTCCATACTCACTTGCTGATTCGCCAACAACACACCCTT
AAA CAGTC-YYY-3';
and

[SEQ ID NO: 9]
5'-XXX-CCGAAACCAGACCACCCCACCAAGGCCACTCGGTCGAACCGC
CAACACT CAC-YYY-3'.

Nonglycated: Human Serum Albumin (HSA) Aptamers:
                                         [SEQ ID NO: 10]
5'-XXX-CTCTCCGGCCGCTGACCCAGTTTGGAGGGGGAGGAGGCCGGG
C-YYY-3';

[SEQ ID NO: 11]
5'-XXX-ACGGGCACTGGTTCCATCCGCATGAGATTGATGTGTCAACTTA
T-YYY-3';

[SEQ ID NO: 12]
5'-XXX-CAATACCGATTGTTCTAAGGGAAAACGTGTAACTTTGGATCCT
T-YYY-3';

[SEQ ID NO: 13]
5'-XXX-TAGCGACACACGTGGCCGCTGGTTGCCGGGCGCCACGGATCCT
T-YYY-3';

[SEQ ID NO: 14]
5'-XXX-CCAGCTCGTAGTGGCGTCTTTTTTTCATTTGGTACTTATCGCA
A -YYY-3';
and

[SEQ ID NO: 15]
5'-XXX-AAATTTCATGTTCCCACACGTTCCATGCGCCCTCCTTCGAGTG
C-YYY-3'.
```

Example 5

Surface Functionalization Method Using SAMs for Optimizing Sensitivity and Selectivity Based on Target Characteristics The sensitivity and selectivity of the binary SAM formation for aptamer mobilization may be further enhanced. For example, to control the linking spacing and the distance between the aptamer and SPR surface, two different types of self-assembling thiol molecules are deposited on the surface. A 1 mM ethanol solution of 11-mercaptoundecanoic acid ($SH-(CH_2)_5-COOH$, MUA) and mercaptopropanol ($SH-(CH_2)_2-OH$, MPL) are prepared separately. Each solution is mixed at a 1:1 volume ratio while keeping the total concentration of the two components at 1 mM. A binary SAM of MUA and MPL is formed on a gold surface by soaking the gold surface in the mixed thiol solution for 1 hr. Then, the gold surface is subsequently rinsed with ethanol and DI water.

MPL density can be controlled for optimum signal transfer by applying an electric potential to the gold surface in 0.5 M KOH solution (pH 13). The applied potential of −0.5~−1.0 V for 30 min detaches portion of MPL, resulting in a less dense MPL layer that enhances signal transfer. Then, the surface is immediately washed by DI water.

After the surface is dried, then it is treated with a solution of N-hydroxysuccinimide (NHS) and N-(3-dimethylamnopropyl)-N-ethylcarbodiimide hydrochloride (EDC) (NHS 0.2M, EDC 0.05M) for 30 min to activate the carboxyl group of MUA. The surface is then washed with DI water and then immersed in the 5 μM aptamer solution. Aptamers are covalently attached to the activated MUA. Finally, the surface is rinsed with the PBS buffer.

This surface functionalization method is applicable not only for SPR, but also to optimize the sensitivity and selectivity of other sensing modalities such as Raman and fluorescence spectroscopy. The method can be used to improve the performance of existing monitoring technologies.

Example 6

Methods for Reducing Effects of Confounding Substances Present in Samples

As part of the functionalization process, the MPL layer is hydrophilic in nature. This property can prevent the non-specific adsorption of proteins to the surface. In another embodiment, the aptamer recognition element can be extended beyond the normal SPR sensing range (while still maintaining a desired sensitivity) through an extended linking approach. In this embodiment, multiple linkages can be obtained through terminations, such as for thiols. Between the terminations, gold nanoparticle interfaces can be made by exposing the surface to a gold nanoparticle solution. This nanoparticle coupling can allow the aptamer binding response to be detected by the SPR sensor at separation distances beyond the normal SPR detection limit.

It is to be noted that, as in the non-aptamer locations, densely packed linkages of lengths outside the SPR range can be made that are void of metal particle coupling. Therefore, if non-specific protein adsorption or other confounding components are encountered in these locations, a corresponding SPR response will not occur, thereby improving the selectivity performance for the sensor.

In another embodiment, a secondary physical vapor deposition (PVD) can be formed over subsequent MPA layers, followed by thermal treatment to obtain a similar structure to extend the aptamers away from the SPR foundation surface, while maintaining sensitivity through the metal coupling linkages.

Example 7

Biomarker Detection

The method and platform described herein are also useful in the field of biomarker detection for disease diagnosis and assessment.

For example, for the proteins described herein (e.g., glycated proteins), the accurate detection can facilitate the treatment of diabetes and help minimize the numerous associated healthcare conditions, such as increased risk of cardiovascular disease, blindness, kidney failure, and many others.

The method and platform herein can be miniaturized so as to be easily integrated into a handheld device, thus allowing the method and/or platform to be used directly in physician offices, in the home, or in the field.

The measurements of glycated proteins (which are a measure of glycemic compliance), instead of being only available during physician examinations through untimely offsite analysis, are thus readily available to the patient or healthcare giver in a more readily assessable manner. These more widely accessible measurements would, in turn, provide complimentary information to that of self-monitoring blood glucose measurements to further help diabetics better manage their condition and mitigate potential long term health complications.

Furthermore, if such information is available on a more frequent basis with expanded historic time windows, this could significantly impact the understanding of glucose regulation within and outside the diabetic community, which could lead to a better understanding of glycemic control through the development, education, and training of new and/or optimized therapeutic approaches to diabetes.

Example 8

Kits

The sensor described herein can be provided in the form of kits of parts. Such kits include but are not limited to diagnostic kits, biomarker discovery kits, environmental testing kits, biohazard or bioweapons detection kits, and kits for detecting targets in medical or analytical chemistry applications. By way of non-limiting example, the amine-terminated aptamers can be included as a molecule alone or already attached to a substrate. Additional components can also be included and comprise microfluidic chip, reference standards, and additional components identifiable by a skilled person upon reading of the present disclosure. Also, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A method for forming a sensor for one or more analytes, comprising:
   a) adsorbing binary components comprised of 3-mercaptopropionic acid (MPA) and (1-mercapto-11-undecyl)tri(ethylene glycol) (PEG3) on a substrate;
   b) reductively desorbing MPA from the substrate of step a);
   c) forming a dithiobis-N-succinimidyl propionate (DTSP) layer on the substrate of step b);
   d) immobilizing at least one type of aptamer on the substrate of step c); and,
   e) removing unbound aptamer from the PEG3 on the substrate of step d), thus leaving aptamer attached to the DTSP layer of the substrate.

2. The method of claim 1,
   wherein, in step a) the substrate is a gold surface substrate in an ethanol solution;
   wherein, in step b) the MPA is desorbed from the substrate of step a) in a 0.5 M KOH solution, wherein the adsorbed MPA in a phase-separated binary self-assembled monolayer (SAM) of MPA and PEG3 is selectively reduced by applying a potential of −1.2 V for 30 min to the solution; and,
   wherein, in step c) the DTSP is formed by immersing the substrate of step b) having the PEG3 layer thereon, in a 1 mM DTSP solution to form the DTSP layer thereon.

3. The method of claim 1, wherein the analyte comprises a glycated form of a protein in blood.

4. The method of claim 3, comprising determining a fraction of a specific glycated protein from a total serum protein level.

5. The method of claim 1, wherein the analyte comprises one or more of: human hemoglobin, albumin, including human serum albumin (HSA), immunoglobulin G (IgG), immunoglobulin M (IgM), fibrinogen, and/or fragments thereof, the analyte being in glycated or non-glycated forms.

6. The method of claim 1, wherein the analytes comprise at least a first analyte having a different half-life from at least a second analyte, and the method further comprises quantifying the first and second analytes to provide a retrospective judgment regarding levels of the first and second analytes over one or more time periods.

7. The method of claim 1, wherein the analytes comprise at least a first analyte, at least a second analyte, and at least a third analyte, each of the first, second, and third analytes having different half-lives; the method further comprising: quantifying the first, second, and third analytes to provide a retrospective judgment regarding levels of the first, second, and third analytes over one or more time periods.

8. The method of claim 7, wherein the first analyte is comprised of hemoglobin, the second analyte is comprised of IgM, and the third analyte is comprised of albumin; wherein one or more of the first analyte, the second analyte or the third analyte is present in a glycated form or a non-glycated form.

9. The method of claim 1, the method further comprising: contacting the sensor with a blood sample; determining an amount of a glycated form of the analyte in the blood; and correlating the amount of the analyte present in the blood sample in the glycated form to a control level for a given time frame.

10. The method of claim 9, wherein the amount of the glycated form of the protein is determined using surface plasmon resonance (SPR).

* * * * *

SEQUENCE LISTING

```
<160> NUMBER OF SEQ ID NOS: 15

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NH2-(CH2)6

<400> SEQUENCE: 1
ggttggtgtg gttgg                                                        15

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-NH2-(CH2)6

<400> SEQUENCE: 2
```
ctatcagtcc gtggtagggc aggttggggt gact                        34

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-SH-(CH2)6

<400> SEQUENCE: 3
ccgaaaccag accaccccac caaggccact cggtcgaacc gccaacactc acccca       56

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atccttcatc ccatggttgc atattgattg ccggttcctt aaat              44

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agggaaaggt gtgggttagg agcttgaaat cgaaagagg ggcg               44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttagcgagct gcacacacaa tggactcgtc ataccgtgct gttt              44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atctgcagaa ttcgcccttg ctggtgcagt acacacccgg cggg              44

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctcactccat actcacttgc tgattcgcca acaacacacc cttaaacagt c        51

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccgaaaccag accaccccac caaggccact cggtcgaacc gccaacactc ac        52

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctctccggcc gctgacccag tttggagggg ggaggaggcc gggc                 44

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acgggcactg gttccatccg catgagattg atgtgtcaac ttat                 44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caataccgat tgttctaagg gaaaacgtgt aactttggat cctt                 44

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tagcgacaca cgtggccgct ggttgccggg cgccacggat cctt                 44

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

-continued

```
ccagctcgta gtggcgtctt tttttcattt ggtacttatc gcaa                44

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaatttcatg ttcccacacg ttccatgcgc cctccttcga gtgc                44
```